US012626812B2

(12) United States Patent
Moctezuma de la Barrera et al.

(10) Patent No.: US 12,626,812 B2
(45) Date of Patent: May 12, 2026

(54) SYSTEM AND METHOD FOR ARRANGING OBJECTS IN AN OPERATING ROOM IN PREPARATION FOR SURGICAL PROCEDURES

(71) Applicant: Stryker Corporation, Kalamazoo, MI (US)

(72) Inventors: José Luis Moctezuma de la Barrera, Freiburg (DE); Donald W. Malackowski, Schoolcraft, MI (US)

(73) Assignee: Stryker Corporation, Portage, MI (US)

( * ) Notice: Subject to any disclaimer, the term of this patent is extended or adjusted under 35 U.S.C. 154(b) by 280 days.

(21) Appl. No.: 17/510,527

(22) Filed: Oct. 26, 2021

(65) Prior Publication Data

US 2022/0044795 A1     Feb. 10, 2022

Related U.S. Application Data

(60) Continuation of application No. 16/447,422, filed on Jun. 20, 2019, now Pat. No. 11,183,297, which is a
(Continued)

(51) Int. Cl.
*G16H 40/40* (2018.01)
*A61B 17/15* (2006.01)
(Continued)

(52) U.S. Cl.
CPC ........... *G16H 40/40* (2018.01); *A61B 17/154* (2013.01); *A61B 17/17* (2013.01);
(Continued)

(58) Field of Classification Search
CPC .............. A61B 17/154; A61B 17/1742; A61B 17/1764
See application file for complete search history.

(56) References Cited

U.S. PATENT DOCUMENTS

| | | | |
|---|---|---|---|
| 4,442,493 A | 4/1984 | Wakai et al. | |
| 4,979,949 A | 12/1990 | Matsen, III et al. | |

(Continued)

FOREIGN PATENT DOCUMENTS

| | | | |
|---|---|---|---|
| CN | 1985773 A | 6/2007 | |
| CN | 102393739 A | 3/2012 | |

(Continued)

OTHER PUBLICATIONS

English language abstract for JP 2000-139948 A extracted from espacenet.com database on Nov. 3, 2021, 2 pages.
(Continued)

*Primary Examiner* — Sameh R Boles
(74) *Attorney, Agent, or Firm* — Howard & Howard Attorneys PLLC

(57) ABSTRACT

Systems, methods and software guide arrangement of a robotic system in an operating room. Controller(s) evaluate surgical procedure information and determine a desired placement of the robotic system in the operating room based on evaluation of the surgical procedure information. A localizer determines a current placement of the robotic system in the operating room. A display provides visual representations of the current placement and the desired placement of the robotic system to guide a user on manual placement of the robotic system in the operating room.

10 Claims, 10 Drawing Sheets

Related U.S. Application Data division of application No. 15/591,343, filed on May 10, 2017, now Pat. No. 10,410,746, which is a continuation of application No. 14/203,663, filed on Mar. 11, 2014, now Pat. No. 9,652,591.

(60) Provisional application No. 61/779,725, filed on Mar. 13, 2013.

(51) Int. Cl.
*A61B 17/17* (2006.01)
*A61B 34/20* (2016.01)
*A61B 34/00* (2016.01)
*A61B 34/10* (2016.01)

(52) U.S. Cl.
CPC ...... *A61B 17/1742* (2013.01); *A61B 17/1764* (2013.01); *A61B 34/20* (2016.02); *A61B 2034/105* (2016.02); *A61B 2034/107* (2016.02); *A61B 2034/2055* (2016.02); *A61B 2034/252* (2016.02)

(56) References Cited

U.S. PATENT DOCUMENTS

| | | | |
|---|---|---|---|
| 5,078,140 A | 1/1992 | Kwoh | |
| 5,086,401 A | 2/1992 | Glassman et al. | |
| 5,091,861 A | 2/1992 | Geller et al. | |
| 5,154,717 A | 10/1992 | Matsen, III | |
| 5,279,309 A | 1/1994 | Taylor et al. | |
| 5,299,288 A | 3/1994 | Glassman et al. | |
| 5,343,391 A | 8/1994 | Mushabac | |
| 5,397,323 A | 3/1995 | Taylor et al. | |
| 5,399,951 A | 3/1995 | Lavallee et al. | |
| 5,408,409 A | 4/1995 | Glassman et al. | |
| 5,544,282 A | 8/1996 | Chen et al. | |
| 5,562,448 A | 10/1996 | Mushabac | |
| 5,569,578 A | 10/1996 | Mushabac | |
| 5,630,431 A | 5/1997 | Taylor | |
| 5,682,886 A | 11/1997 | Delp et al. | |
| 5,695,500 A | 12/1997 | Taylor et al. | |
| 5,730,129 A | 3/1998 | Darrow et al. | |
| 5,748,767 A | 5/1998 | Raab | |
| 5,769,092 A | 6/1998 | Williamson, Jr. | |
| 5,776,136 A | 7/1998 | Sahay et al. | |
| 5,784,542 A | 7/1998 | Ohm et al. | |
| 5,792,135 A | 8/1998 | Madhani et al. | |
| 5,792,147 A | 8/1998 | Evans et al. | |
| 5,806,518 A | 9/1998 | Mittelstadt | |
| 5,807,377 A | 9/1998 | Madhani et al. | |
| 5,815,640 A | 9/1998 | Wang et al. | |
| 5,820,623 A | 10/1998 | Ng | |
| 5,824,085 A | 10/1998 | Sahay et al. | |
| 5,871,018 A | 2/1999 | Delp et al. | |
| 5,880,976 A | 3/1999 | DiGioia, III et al. | |
| 5,882,206 A | 3/1999 | Gillio | |
| 5,891,157 A | 4/1999 | Day et al. | |
| 5,950,629 A | 9/1999 | Taylor et al. | |
| 5,952,796 A | 9/1999 | Colgate et al. | |
| 5,971,976 A | 10/1999 | Wang et al. | |
| 5,976,156 A * | 11/1999 | Taylor .................... A61B 34/20 606/130 | |
| 5,995,738 A | 11/1999 | DiGioia, III et al. | |
| 6,002,859 A | 12/1999 | DiGioia, III et al. | |
| 6,033,415 A | 3/2000 | Mittelstadt et al. | |
| 6,037,927 A | 3/2000 | Rosenberg | |
| 6,063,095 A | 5/2000 | Wang et al. | |
| 6,097,168 A | 8/2000 | Katoh et al. | |
| 6,102,850 A | 8/2000 | Wang et al. | |
| 6,157,873 A | 12/2000 | DeCamp et al. | |
| 6,205,411 B1 | 3/2001 | DiGioia, III et al. | |
| 6,228,089 B1 | 5/2001 | Wahrburg | |
| 6,233,504 B1 | 5/2001 | Das et al. | |
| 6,236,875 B1 | 5/2001 | Bucholz et al. | |
| 6,236,906 B1 | 5/2001 | Muller | |
| 6,304,050 B1 | 10/2001 | Skaar et al. | |
| 6,311,100 B1 | 10/2001 | Sarma et al. | |
| 6,314,312 B1 | 11/2001 | Wessels et al. | |
| 6,322,567 B1 | 11/2001 | Mittelstadt et al. | |
| 6,329,778 B1 | 12/2001 | Culp et al. | |
| 6,330,837 B1 | 12/2001 | Charles et al. | |
| 6,336,931 B1 | 1/2002 | Hsu et al. | |
| 6,341,231 B1 | 1/2002 | Ferre et al. | |
| 6,347,240 B1 | 2/2002 | Foley et al. | |
| 6,351,659 B1 | 2/2002 | Vilsmeier | |
| 6,351,661 B1 | 2/2002 | Cosman | |
| 6,366,796 B1 | 4/2002 | Yanof et al. | |
| 6,368,330 B1 | 4/2002 | Hynes et al. | |
| 6,377,839 B1 | 4/2002 | Kalfas et al. | |
| 6,385,475 B1 | 5/2002 | Cinquin et al. | |
| 6,385,509 B2 | 5/2002 | Das et al. | |
| 6,408,253 B2 | 6/2002 | Rosenberg et al. | |
| 6,413,264 B1 | 7/2002 | Jensen et al. | |
| 6,414,711 B2 | 7/2002 | Arimatsu et al. | |
| 6,421,048 B1 | 7/2002 | Shih et al. | |
| 6,423,077 B2 | 7/2002 | Carol et al. | |
| 6,430,434 B1 | 8/2002 | Mittelstadt | |
| 6,432,112 B2 | 8/2002 | Brock et al. | |
| 6,434,415 B1 | 8/2002 | Foley et al. | |
| 6,436,107 B1 | 8/2002 | Wang et al. | |
| 6,450,978 B1 | 9/2002 | Brosseau et al. | |
| 6,461,372 B1 | 10/2002 | Jensen et al. | |
| 6,466,815 B1 | 10/2002 | Saito et al. | |
| 6,473,635 B1 | 10/2002 | Rasche | |
| 6,490,467 B1 | 12/2002 | Bucholz et al. | |
| 6,491,702 B2 | 12/2002 | Heilbrum et al. | |
| 6,494,882 B1 | 12/2002 | Leboultz et al. | |
| 6,501,997 B1 | 12/2002 | Kiakino | |
| 6,514,082 B2 | 2/2003 | Kaufman et al. | |
| 6,520,228 B1 | 2/2003 | Kennedy et al. | |
| 6,522,906 B1 | 2/2003 | Salisbury, Jr. et al. | |
| 6,533,737 B1 | 3/2003 | Brosseau et al. | |
| 6,535,756 B1 | 3/2003 | Simon et al. | |
| 6,542,770 B2 | 4/2003 | Zylka et al. | |
| 6,620,174 B2 | 9/2003 | Jensen et al. | |
| 6,665,554 B1 | 12/2003 | Charles et al. | |
| 6,676,669 B2 | 1/2004 | Charles et al. | |
| 6,699,177 B1 | 3/2004 | Wang et al. | |
| 6,704,694 B1 | 3/2004 | Basdogan et al. | |
| 6,711,432 B1 | 3/2004 | Krause et al. | |
| 6,723,106 B1 | 4/2004 | Charles et al. | |
| 6,728,599 B2 | 4/2004 | Wang et al. | |
| 6,757,582 B2 | 6/2004 | Brisson et al. | |
| 6,778,867 B1 | 8/2004 | Ziegler et al. | |
| 6,785,572 B2 | 8/2004 | Yanof et al. | |
| 6,785,593 B2 | 8/2004 | Wang et al. | |
| 6,788,999 B2 | 9/2004 | Green | |
| 6,793,653 B2 | 9/2004 | Sanchez et al. | |
| 6,804,547 B2 | 10/2004 | Pelzer et al. | |
| 6,827,723 B2 | 12/2004 | Carson | |
| 6,837,892 B2 | 1/2005 | Shoham | |
| 6,871,117 B2 | 3/2005 | Wang et al. | |
| 6,892,112 B2 | 5/2005 | Wang et al. | |
| 6,963,792 B1 | 11/2005 | Green | |
| 6,978,166 B2 | 12/2005 | Foley et al. | |
| 6,999,852 B2 | 2/2006 | Green | |
| 7,006,895 B2 | 2/2006 | Green | |
| 7,035,716 B2 | 4/2006 | Harris et al. | |
| 7,055,789 B2 | 6/2006 | Libbey et al. | |
| 7,056,123 B2 | 6/2006 | Gregorio et al. | |
| 7,097,640 B2 | 8/2006 | Wang et al. | |
| 7,139,601 B2 | 11/2006 | Bucholz et al. | |
| 7,155,316 B2 | 12/2006 | Sutherland et al. | |
| 7,181,315 B2 | 2/2007 | Watanabe et al. | |
| 7,204,844 B2 | 4/2007 | Jensen et al. | |
| 7,206,626 B2 | 4/2007 | Quaid, III | |
| 7,206,627 B2 | 4/2007 | Abovitz et al. | |
| 7,215,326 B2 | 5/2007 | Rosenberg | |
| 7,239,940 B2 | 7/2007 | Wang et al. | |
| 7,249,951 B2 | 7/2007 | Bevirt et al. | |
| 7,302,288 B1 * | 11/2007 | Schellenberg ......... A61B 34/20 606/130 | |
| 7,346,417 B2 | 3/2008 | Luth et al. | |

(56) References Cited

U.S. PATENT DOCUMENTS

| | | | |
|---|---|---|---|
| 7,348,747 | B1 | 3/2008 | Theobold et al. |
| 7,404,716 | B2 | 7/2008 | Gregorio et al. |
| 7,454,268 | B2 | 11/2008 | Jinno |
| 7,466,303 | B2 | 12/2008 | Yi et al. |
| 7,468,594 | B2 | 12/2008 | Svensson et al. |
| 7,543,588 | B2 | 6/2009 | Wang et al. |
| 7,573,461 | B2 | 8/2009 | Rosenberg |
| 7,625,383 | B2 | 12/2009 | Charles et al. |
| 7,648,513 | B2 | 1/2010 | Green et al. |
| 7,660,623 | B2 | 2/2010 | Hunter et al. |
| 7,683,565 | B2 | 3/2010 | Quaid, III et al. |
| 7,725,162 | B2 | 5/2010 | Malackowski et al. |
| 7,744,608 | B2 | 6/2010 | Lee et al. |
| 7,747,311 | B2 | 6/2010 | Quaid, III |
| 7,813,838 | B2 | 10/2010 | Sommer |
| 7,818,044 | B2 | 10/2010 | Dukesherer et al. |
| 7,824,424 | B2 | 11/2010 | Jensen et al. |
| 7,831,292 | B2 | 11/2010 | Quaid et al. |
| 7,835,784 | B2 | 11/2010 | Mire et al. |
| 7,892,243 | B2 | 2/2011 | Stuart |
| 7,914,522 | B2 | 3/2011 | Morley et al. |
| 7,950,306 | B2 | 5/2011 | Stuart |
| 8,010,180 | B2 | 8/2011 | Quaid et al. |
| 8,035,487 | B2 | 10/2011 | Malackowski |
| 8,219,177 | B2 | 7/2012 | Smith et al. |
| 8,287,522 | B2 | 10/2012 | Moses et al. |
| 8,428,781 | B2 | 4/2013 | Chang et al. |
| 8,548,779 | B2 | 10/2013 | Ortmaier et al. |
| 8,548,822 | B2 | 10/2013 | Moctezuma de la Barrera |
| 8,977,394 | B2 | 3/2015 | Khoukhi et al. |
| 9,259,282 | B2 | 2/2016 | Azizian et al. |
| 9,381,085 | B2 | 7/2016 | Axelson, Jr. et al. |
| 9,615,987 | B2 | 4/2017 | Worm et al. |
| 9,652,591 | B2 | 5/2017 | Moctezuma de la Barrera et al. |
| 9,668,768 | B2 | 6/2017 | Piron et al. |
| 9,707,043 | B2 | 7/2017 | Bozung |
| 10,410,746 | B2 | 9/2019 | Moctezuma de la Barrera et al. |
| 2002/0035321 | A1 | 3/2002 | Bucholz et al. |
| 2003/0208296 | A1 | 11/2003 | Brisson et al. |
| 2004/0010190 | A1 | 1/2004 | Shahidi |
| 2004/0024311 | A1 | 2/2004 | Quaid |
| 2004/0034283 | A1 | 2/2004 | Quaid |
| 2004/0034302 | A1 | 2/2004 | Abovitz et al. |
| 2004/0077939 | A1 | 4/2004 | Graumann |
| 2004/0106916 | A1 | 6/2004 | Quaid et al. |
| 2005/0096535 | A1 | 5/2005 | Moctezuma de la Barrera |
| 2006/0109266 | A1 | 5/2006 | Itkowitz et al. |
| 2006/0142657 | A1 | 6/2006 | Quaid et al. |
| 2006/0155262 | A1 | 7/2006 | Kishi et al. |
| 2006/0161052 | A1 | 7/2006 | Colombet |
| 2006/0176242 | A1 | 8/2006 | Jaramaz et al. |
| 2006/0229766 | A1 | 10/2006 | Setsuda |
| 2007/0073136 | A1 | 3/2007 | Metzger |
| 2007/0260394 | A1 | 11/2007 | Dean |
| 2007/0265527 | A1 | 11/2007 | Wohlgemuth |
| 2007/0270685 | A1 | 11/2007 | Kang et al. |
| 2008/0058776 | A1 | 3/2008 | Jo et al. |
| 2008/0077158 | A1 | 3/2008 | Haider et al. |
| 2008/0161829 | A1 | 7/2008 | Kang |
| 2009/0003975 | A1 | 1/2009 | Kuduvalli et al. |
| 2009/0192519 | A1 | 7/2009 | Omori |
| 2010/0331859 | A1 | 12/2010 | Omori |
| 2011/0015649 | A1 | 1/2011 | Anvari et al. |
| 2011/0069867 | A1 | 3/2011 | Buehner |
| 2011/0106102 | A1 | 5/2011 | Balicki et al. |
| 2011/0130761 | A1 | 6/2011 | Plaskos et al. |
| 2011/0152676 | A1 | 6/2011 | Groszmann et al. |
| 2011/0190790 | A1 | 8/2011 | Summerer et al. |
| 2011/0263971 | A1 | 10/2011 | Nikou et al. |
| 2011/0264107 | A1 | 10/2011 | Nikou et al. |
| 2011/0275957 | A1 | 11/2011 | Bhandari |
| 2012/0059378 | A1 | 3/2012 | Farrell |
| 2012/0071752 | A1 | 3/2012 | Sewell et al. |
| 2012/0071893 | A1 | 3/2012 | Smith et al. |
| 2012/0101508 | A1* | 4/2012 | Wook Choi .......... B25J 9/1697 |
| | | | 700/259 |
| 2012/0143084 | A1 | 6/2012 | Shoham |
| 2013/0019883 | A1 | 1/2013 | Worm et al. |
| 2013/0060278 | A1 | 3/2013 | Bozung et al. |
| 2013/0096574 | A1 | 4/2013 | Kang et al. |
| 2013/0211419 | A1 | 8/2013 | Jensen |
| 2013/0211792 | A1 | 8/2013 | Kang et al. |
| 2014/0052153 | A1 | 2/2014 | Griffiths et al. |
| 2017/0239000 | A1 | 8/2017 | Moctezuma de la Barrera et al. |
| 2018/0263670 | A1 | 9/2018 | Moctezuma De la Barrera et al. |
| 2019/0069962 | A1 | 3/2019 | Tabandeh et al. |
| 2019/0192249 | A1 | 6/2019 | Bowling et al. |
| 2019/0304602 | A1 | 10/2019 | Moctezuma de la Barrera et al. |

FOREIGN PATENT DOCUMENTS

| | | |
|---|---|---|
| CN | 202453770 U | 9/2012 |
| EP | 1462224 A2 | 9/2004 |
| EP | 1471402 A2 | 10/2004 |
| EP | 1523950 A1 | 4/2005 |
| EP | 1571581 A1 | 9/2005 |
| JP | 2000139948 A | 5/2000 |
| JP | 2011502672 A | 1/2011 |
| WO | 199611624 A2 | 4/1996 |
| WO | 1999037220 A1 | 7/1999 |
| WO | 2000021450 A1 | 4/2000 |
| WO | 2000035366 A1 | 6/2000 |
| WO | 2000059397 A1 | 10/2000 |
| WO | 2000060571 A1 | 10/2000 |
| WO | 200200131 A1 | 1/2002 |
| WO | 2002024051 A2 | 3/2002 |
| WO | 2002060653 A2 | 8/2002 |
| WO | 2002065931 A1 | 8/2002 |
| WO | 2002074500 A2 | 9/2002 |
| WO | 2002076302 A2 | 10/2002 |
| WO | 2003064116 A2 | 8/2003 |
| WO | 2003094108 A2 | 11/2003 |
| WO | 2004001569 A2 | 12/2003 |
| WO | 2004014244 A2 | 2/2004 |
| WO | 2004019785 A2 | 3/2004 |
| WO | 2004069036 A2 | 8/2004 |
| WO | 2005009215 A2 | 2/2005 |
| WO | 2006058633 A1 | 6/2006 |
| WO | 2006063156 A1 | 6/2006 |
| WO | 2007017642 A1 | 2/2007 |
| WO | 2007111749 A2 | 10/2007 |
| WO | 2007117297 A2 | 10/2007 |
| WO | 2007136739 A2 | 11/2007 |
| WO | 2007136768 A2 | 11/2007 |
| WO | 2007136769 A2 | 11/2007 |
| WO | 2007136771 A2 | 11/2007 |
| WO | 2009059330 A2 | 5/2009 |
| WO | 2011021192 A1 | 2/2011 |
| WO | 2011088541 A1 | 7/2011 |
| WO | 2011106861 A1 | 9/2011 |
| WO | 2011113483 A1 | 9/2011 |
| WO | 2011128766 A2 | 10/2011 |
| WO | 2011133873 A1 | 10/2011 |
| WO | 2011133927 A1 | 10/2011 |
| WO | 2011134083 A1 | 11/2011 |
| WO | 2012018816 A2 | 2/2012 |
| WO | 2013142997 A1 | 10/2013 |

OTHER PUBLICATIONS

A. Ansara; D. Rodrigues; J.P. Desai; K. Daniilidis; V. Kumar; M. F.M. Campos, Visual and haptic collaborative tele-presence, Computers & Graphics, 2001, pp. 789-798, vol. 25, Elsevier, Inc.; 10 pages.

A.E. Quaid, III; R.A. Abovitz, Haptic Information Displays for Computer-Assisted Surgery, Robotics and Automation, 2002 Proceedings. ICRA '02. IEEE International Conference on, May 2002, pp. 2092-2097, vol. 2, IEEE, Washington DC, USA; 6 pages.

A.M. Digioia, III; B. Jaramaz; B. D. Colgan, Computer Assisted Orthopaedic Surgery Image Guided and Robotic Assistive Technologies, Clinical Orthopaedics & Related Research:, Sep. 1998,

(56) References Cited

OTHER PUBLICATIONS pp. 8-16, vol. 354, Lippincott Williams & Wilkins, Pitsburgh, PA, USA; 9 pages.

AchieveCAS Diz Computer Assisted Surgery, Smith & Nephew, Surgical Technique, Version 2.1, Sep. 2007, Orthopaedic Reconstruction, Smith & Nephew, Inc., Memphis, TN, USA; 29 pages.

Aesculap Orthopaedics e.motion, Knee Endoprosthesis System, Navigated Surgical Technique, B | Braun Sharing Expertise, e.motion® TKA 4.2, Aesculap AG & Co. KG, Jan. 6, 2014, Brochure No. O 248 02; 58 pages.

B. Davies, A review of robotics in surgery, Proceedings of the Institution of Mechanical Engineers, Part H: Journal of Engineering in Medicine Jan. 1, 2000, vol. 214, No. 1, pp. 129-140, Sage Publications; 13 pages.

B. Davies, Computer-assisted and robotics surgery, International Congress and Symposium Series 223, 1997, pp. 71-82, Royal Society of Medicine Press Limited; 12 pages.

B. Jaramaz; C. Nikou; D.A. Simon; A.M. Digioia III, Range of Motion After Total Hip Arthroplasty Experimental Verification of the Analytical Simulator, CVRMed-MRCAS'97, Lecture Notes in Computer Science, Feb. 20, 1997, pp. 573-582, vol. 1205, Springer Berlin Heidelberg, Pittsburgh, PA, USA; 14 pages.

B. Preising; CA Davis; T.C. Hsia and B. Mittelstadt, A Literature Review Robots in Medicine, Engineering in Medicine and Biology Magazine, IEEE (vol. 10, Issue: 2), Jun. 1991, pp. 13-22, IEEE; 10 pages.

B.K. Redlich; C. Burghart; R. Krempien; T. Redlich; A. Pernozzoli; H. Grabowski; J. Muenchenberg; J. Albers; S. Hafeld; C. Vahl; U. Rembold; H. Woern, Robot assisted craniofacial surgery first clinical evaluation, Computer Assisted Radiology and Surgery, 1999, pp. 828-833; 7 pages.

B.L. Davies, Robotics in minimally invasive surgery, Through the Keyhole: Microengineering in Minimally Invasive Surgery, IEE Colloquium on, Jun. 6, 1995, p. 5/1-5/2, London, UK; 2 pages.

B.L. Davies; K.L. Fan; R.D. Hibberd; M. Jakopec; S.J. Harris, Acrobot—using robots and surgeons synergistically in knee surgery, Advanced Robotics, 1997. ICAR '97. Proceedings., 8th International Conference on, Jul. 7-9, 1997, pp. 173-178, IEEE, Monterey, CA, USA; 6 pages.

B.L. Davies; S.J. Harris; W.J. Lin; R.D. Hibberd; R. Middleton; J.C. Cobb, Active compliance in robotic surgery—the use of force control as a dynamic constraint, Proceedings of the Institution of Mechanical Engineers, Part H: Journal of Engineering in Medicine, Apr. 1, 1997, pp. 285-292, vol. 211, Sage; 9 pages.

C. Burghart; J. Keitel; S. Hassfeld; U. Rembold; H. Woern, Robot Controlled Osteotomy in Craniofacial Surgery, First International Workshop on Haptic Devices in Medical Applications Proceedings, Jun. 23, 1999, pp. 12-22, Paris, FR; 13 pages.

C. Doignon; F. Nageotte; M. De Mathelin, Segmentation and guidance of multiple rigid objects for intra-operative endoscopic vision, Proceeding WDV'05/WDV'06/ICCV'05/ECCV'06 Proceedings of the 2005/2006 International Conference on Dynamical Vision, 2006, pp. 314-327, Springer-Verlag Berlin, Heidelberg, Illkirch, FR; 14 pages.

C. Meng; T. Wang; W. Chou; S. Luan; Y. Zhang; Z. Tian, Remote surgery case robot-assisted teleneurosurgery, Robotics and Automation, 2004. Proceedings. ICRA '04. 2004 IEEE International Conference on, Apr. 26-May 1, 2004, pp. 819-823, vol. 1, IEEE, New Orleans, LA, USA; 5pages.

C. Sim; S.N. Wan; Y.T. Ming; L. Yong-Chong; T.Y. Tseng, Image-Guided Manipulator Compliant Surgical Planning Methodology for Robotic Skull-Base Surgery, Medical Imaging and Augmented Reality, 2001. Proceedings. International Workshop on, Jun. 10-12, 2001, pp. 26-29, IEEE, Shatin, HK; 4 pages.

C.B. Zilles; J.K. Salisbury, A Constraint-Based God-object Method for Haptic Display, Intelligent Robots and Systems 95. 'Human Robot Interaction and Cooperative Robots', Proceedings. 1995 IEEE/RSJ International Conference on , Aug. 5-9, 1995, pp. 146-151, vol. 3, IEEE, MIT, Cambridge, MA, USA; 6 pages.

C.N. Riviere and N.V. Thakor, Modeling and Canceling Tremor in Human-Machine Interfaces, Engineering in Medicine and Biology Magazine, IEEE, vol. 15, Issue 3, May/Jun. 1996, pp. 29-36, IEEE; 8 pages.

C.O.R. Grueneis; R.J. Richter; F.F. Hennig, Clinical Introduction of the Caspar System Problems and Initial Results, 4th International Symposium of Computer Assited Orthopaedic Surgery, CAOS'99, Abstracts from CAOS '99, 1999, p. 160, Davos, Switzerland; 1 pages.

C.R. Burghart, Robotergestutzte Osteotomie in der craniofacialen Chirurgie (Robot Clipped osteotomy in craniofacial surgery), Jul. 1, 1999, GCA-Verlag, 2000; 250 pages.

D. A. Simon; R. V. O'Toole; M. Blackwell; F. Morgan; A. M. Digioia; T. Kanade, Accuracy validation in image-guided orthopaedic surgery, In Medical Robotics and Computer Assisted Surgery, 1995, pp. 185-192, Wiley; 8 pages.

D. Engel, J. Raczkowsky and H. Worn, A Safe Robot System for Craniofacial Surgery, Robotics and Automation, 2001. Proceedings 2001 ICRA. IEEE International Conference on (vol. 2), pp. 2020-2024, [vol. Issue Nos.], IEEE; 5 pages.

D. Y. Choi and C. N. Riviere, Flexure-based Manipulator for Active Handheld Microsurgical Instrument, Engineering In Medicine and Biology Society, 2005. Proceedings of the 2005 IEEE Engineering in Medicine and Biology 27th Annual Conference of the Digital Object Identifier, 2005, pp. 5085-5088, IEEE, Shanghai, China, Sep. 1-4, 2005; 4 pages.

E. Bainville, I. Bricault, P. CINQUIN and S. Lavall'ee, Concepts and Methods of Registration for Computer-Integrated Surgery, Computer Assisted Orthopedic Surgery (CAOS), 1999, pp. 15-34, Hogrefe & Huber Publishers Bern; 22 pages.

E. Watanabe; T. Watanabe; S. Manaka; Y. Mayanagi; K. Takakura, Three-Dimensional Digitizer (Neuronavigator); New Equipment for Computed Tomography-Guided Stereotaxic Surgery, Surgical Neurology, Jun. 1987, pp. 543-547, vol. 27, Issue 6, Elsevier Inc., 5 pages.

E.H. Spencer, The ROBODOC Clinical Trial A Robotic Assistant for Total Hip Arthroplasty, Orthopaedic Nursing, Jan.-Feb. 1996, pp. 9-14, vol. 15, Issue 1; 6 pages.

English language abstract and machine-assisted English language translation of Chinese Publication No. CN1985773 A extracted from www.espacenet.com on Aug. 9, 2017; 13 pages.

English language abstract and machine-assisted English translation for CN 102393739 A extracted from espacenet.com database on Feb. 11, 2021, 11 pages.

English language abstract and machine-assisted English translation for CN 202453770 U extracted from espacenet.com database on Jul. 26, 2021, 9 pages.

F. A. Matsen; J.L. Garbini; J.A. Sidles; B. Pratt; D. Baumgarten; R. Kaiura, Robotic Assistance in Orthopaedic Surgery A Proof of Principle Using Distal Femoral Arthroplasty, Clinical Orthopaedic Related Research, Nov. 1993, pp. 178-186, vol. 296; 9 pages.

F. Leitner, F. Picard, R. Minfelde, H.-J. Schulz, P. Cinquin and D. Saragaglia, Computer-Assisted Knee Surgical Total Replacement, CVRMed-MRCAS'97, Lecture Notes in Computer Science vol. 1205, 1997, pp. 629-638, Springer Berlin Heidelberg, Jan. 1, 1997; 10 pages.

G. Brandt, A. Zimolong, L. Carrat, P. Merloz, H.-W. Staudte, S. Lavallee, K. Radermacher, G. Rau, "CRIGOS: A Compact Robot for Image-Guided Orthopedic Surgery," Information Technology in Biomedicine IEEE Transactions on, vol. 3, No. 4, pp. 252-260, Dec. 1999; 9 pages.

G. Brisson, T. Kanade, A. Digioia and B. Jaramaz, Precision Freehand Sculpting of Bone, Medical Image Computing and Computer-Assisted Intervention—MICCAI 2004, Lecture Notes in Computer Science, vol. 3217, Jan. 1, 2004, pp. 105-112, Springer-Verlag Berlin Heidelberg 2004; 8 pages.

G. Van Ham; J. Bellemans; L. Labey; J. Vander Sloten; R. Van Audekercke; G. Van Der Perre; J. De Schutter, Accuracy study on the registration of the tibia by means of an intramedullary rod in robot-assisted total knee arthroplasty, Poster Session—Knee Arthroplasty—Valencia Foyer, 46th Annual Meeting, Orthopaedic Research Society, Mar. 12-15, 2000, Orlando, Florida, Jan. 1, 2010, p. 450; 1 pages.

(56) References Cited

OTHER PUBLICATIONS

G. Van Ham; K. Denis; J. Vander Sloten; R. Van Audekercke; G. Van Der Perre; J. De Schutter; E. Aertbeliën; S. Demey; J. Bellemans, Machining and Accuracy Studies for a Tibial Knee Implant Using a Force-Controlled Robot, Computer Aided Surgery, Feb. 1998, pp. 123-133, vol. 3, Wiley-Liss, Inc., Heverlee BE; 11 pages.

H. A. Paul, W. L. Bargar, B. Mittlestadt, P. Kazanzides, B. Musits, J. Zuhars, P. W. Cain, B. Williamson and F. G. Smith, Robotic Execution of a Surgical Plan, Systems, Man and Cybernetics, 1992., IEEE International Conference on, Oct. 18-21, 1992, pp. 1621-1623, IEEE, Sacramento, California, US; 3 pages.

H. Haider, O.A. Barrera and K.L. Garvin, Minimally Invasive Total Knee Arthroplasty Surgery Through Navigated Freehand Bone Cutting, Journal of Arthroplasty, Jun. 2007, vol. 22, No. 4, pp. 535-542, Elsevier B.V.; 8 pages.

H.A. Paul; B. Mittlestadt; W.L. Bargar; B. Musits; R.H. Taylor; P. Kazanzides; J. Zuhars; B. Williamson; W. Hanson, A Surgical Robot for Total Hip Replacement Surgery, International Conference on Robotics and Automation, 1992, pp. 606-611, IEEE, Nice, FR; 6 pages.

H.A. Paul; W.L. Bargar; B. Mittlestadt; B. Musits; R. H. Taylor; P. Kazanzides; J. Zuhars; B. Williamson; W. Hanson, Development of a Surgical Robot for Cementless Total Hip Arthroplasty, Clinical Orthopaedics and Related Research, Dec. 1992, pp. 57-66, No. 285, Sacramento, CA, USA; 10 pages.

J. Andreas Bærentzen, Octree-based Volume Sculpting, Proc. Late Breaking Hot Topics, IEEE Visualization '98, pp. 9-12, 1998; 4 pages.

J. K. Salisbury, Active Stiffness Control of a Manipulator in Cartesian Coordinates, Decision and Control including the Symposium on Adaptive Processes, 1980 19th IEEE Conference on, Dec. 1980, pp. 95-100, vol. 19, IEEE, Stanford, CA, USA; 7 pages.

J. L. Moctezuma, F. Gosse and H.-J. Schulz, A Computer and Robotic Aided Surgery System for Accomplishing Osteotomies, First International Symposium on Medical Robotics and Computer Assisted Surgery, Sep. 22-24, 1994, Pittsburgh, Pennsylvania, US; 6 pages.

J. Raczkowsky; J. Münchenberg; I. Bertovic; C. Burghart, Ein Robotersystem fur craniomaxillofaciale chirurgische Eingriffe (A robotic system for surgical procedures craniomaxillofaciale), Computer Forsch. Entw., 1999, pp. 24-35, vol. 14, Springer-Verlag; 12 pages.

J. T. Lea, Registration Graphs A Language for Modeling and Analyzing Registration in Image-Guided Surgery, Dec. 1998, Evanston, Illinois, US; 49 pages.

J. Troccaz, M. Peshkin and B. Davies, Guiding systems for computer-assisted surgery introducing synergistic devices and discussing the different approaches, Medical Image Analysis, Jun. 1998, vol. 2, No. 2, pp. 101-119, Elsevier B.V.; 19 pages.

J. Troccaz; S. Lavallee; E. Hellion, A passive arm with dynamic constraints a solution to safety problems in medical robotics, Systems, Man and Cybernetics, 1993. 'Systems Engineering in the Service of Humans', Conference Proceedings., International Conference on, Oct. 17-20, 1993, pp. 166-171, vol. 3, IEEE, Le Touquet, FR; 6 pages.

J. Troccaz; Y. Delnondedieu, Semi-Active Guiding Systems in Surgery. A Two-DOF Prototype of the Passive Arm with Dynamic Constraints (PADyC), Mechatronics, Jun. 1996, pp. 399-421, vol. 6, Issue 4, 1996, Elsevier Ltd., UK; 23 pages.

J.E. Colgate; M.C. Stanley; J.M. Brown, Issues in the Haptic Display of Tool Use, Intelligent Robots and Systems 95. 'Human Robot Interaction and Cooperative Robots', Proceedings. 1995 IEEE/RSJ International Conference on, Aug. 5-9, 1995, pp. 140-145, vol. 3, IEEE, Pittsburgh, PA, USA; 6 pages.

J.T. Lea, D. Watkins, A Mills, M.A. Peshkin, T.C. Kienzle, III and S.D. Stulberg, Registration and immobilization in robot-assisted surgery, Journal of Image Guided Surgery, Computer Aided Surgery, 1995, vol. 1, No. 2, pp. 80-87; 11 pages.

Julio J. Santos-Munné, Michael A. Peshkin , Srdjan Mirkovic , S. David Stulberg , Thomas C. Kienzle III, A Stereotactic/Robotic System for Pedicle Screw Placement, Interactive Technology and the New Paradigm for Healthcare, (Proceedings of the Medicine Meets Virtual Reality III Conference, San Diego, 1995), pp. 326-333, IOS Press and Ohmsha; 8 pages.

K. Bouazza-Marouf; I. Browbank; J.R. Hewit, Robot-assisted invasive orthopaedic surgery, Mechatronics in Surgery, Jun. 1996, pp. 381-397, vol. 6, Issue 4, UK; 17 pages.

K. Hyosig; J.T. Wen, Autonomous Suturing using Minimally Invasive Surgerical Robots, Control Applications, Sep. 25-27, 2000. Proceedings of the 2000 IEEE International Conference on, 2000, pp. 742-747, IEEE, Anchorage, AK, USA; 6 pages.

K. Hyosig; J.T. Wen, EndoBot A Robotic Assistant in Minimally Invasive Surgeries, Robotics and Automation, 2001. Proceedings 2001 ICRA. IEEE International Conference on, Seoul, KR, 2001, pp. 2031-2036, vol. 2, IEEE, Troy, NY, USA; 6 pages.

Kato A., Yoshimine T., Hayakawa T., Tomita Y., Ikeda T., Mitomo M., Harada K., Mogami H., A frameless, armless navigational system for computer-assisted neurosurgery. Technical note, Journal of Neurosurgery, vol. 74, May 1991, pp. 845-849; 5 pages.

L. Davies; S. Starkie; S.J. Harris; E. Agterhuis; V. Paul; L.M. Auer, Neurobot a special-purpose robot for neurosurgery, Robotics and Automation, 2000. Proceedings. ICRA '00. IEEE International Conference on, Apr. 2000, pp. 4103-4108, vol. 4, IEEE, San Francisco, CA, USA; 6 pages.

P. Nolte, L. Zamorano, S. Jiang, Q. Wang, F. Longlotz, E. Arm and H. Visarius, A Novel Approach to Computer Assisted Spine Surgery, Proc. First International Symposium on Medical Robotics and Computer Assisted Surgery, Pittsburgh, 1994, pp. 323-328; 7 pages.

M. Fadda, D. Bertelli, S. Martelli, M. Marcacci, P. Dario, C. Paggetti, D. Caramella and D. Trippi, Computer Assisted Planning for Total Knee Arthroplasty, pp. 619-628; 10 pages.

M. Fadda, T. Wang, M. Marcacci, S. Martelli, P. Dario, G. Marcenaro, M. Nanetti, C. Paggetti, A. Visani and S. Zaffagnini, Computer-Assisted Knee Arthroplasty at Rizzoli Institutes, First International Symposium on Medical Robotics and Computer Assisted Surgery, Sep. 22-24, 1994, pp. 26-30, Pittsburgh, Pennsylvania, US; 6 pages.

M. Fadda; S. Martelli; P. Dario; M. Marcacci; S. Zaffagnini; A. Visani, Premiers Pas Vers La Dissectomie et la Realisation de Protheses du Genou a L'Aide de Robots, Innov. Tech. Bio. Med. , 1992, pp. 394-409, vol. 13, No. 4; 16 pages.

M. Fleute; S. Lavallee; R. Julliard, Incorporating a statistically based shape model into a system for computer-assisted anterior cruciate ligament surgery, Medical Image Analysis, Oct. 1999, pp. 209-222, vol. 3, No. 3, FR; 14 pages.

M. Jakopec; S.J. Harris; Y B.F. Rodriguez; P. Gomes; J. Cobb; B.L. Davies, The first clinical application of a "hands-on" robotic knee surgery system, Computer Aided Surgery , 2001, pp. 329-339, vol. 6, Issue 6, Wiley-Liss, Inc.; 11 pages.

M. Liebergall; R. Mosheiff; L. Joskowicz; Computer-Aided Orthopaedic Surgery in Skeletal Trauma, Rockwood & Green's Fractures in Adults, 6th Edition, Chapter 23, Lippincott Williams & Wilkins; 60 pages.

Machine-assisted English language abstract for JP 2011-502672 extracted from espacenet.com database on Feb. 12, 2018, 2 pages.

O. Tonet; G. Megali; S. D'Attanasio; P. Dario; M. C. Carrozza; M. Marcacci; S. Martelli; P. F. La Palombara, An Augmented Reality Navigation System for Computer Assisted Arthroscopic Surgery of the Knee, Medical Image Computing and Computer-AssistedIntervention—MICCAI 2000, Lecture Notes in Computer Science, 2000, pp. 1158-1162, vol. 1935, Springer Berlin Heidelberg; 5 pages.

Orto Maquet and Caspar: An Automated Cell for Prosthesis Surgery, Robotics World, Sep./Oct. 1999, pp. 30-31, Circular No. 87 on Reader Reply Card; 2 pages.

P. Kazanzides; J. Zuhars; B. Mittelstadt; B. Williamson; P. Cain; F. Smith; L. Rose; B. Musits, Architecture of a Surgical Robot, Systems, Man and Cybernetics, 1992., IEEE International Conference on, Oct. 18-21, 1992, pp. 1624-1629, vol. 2, IEEE, Chicago, IL, USA; 6 pages.

P. Shinsuk, Safety Strategies for Human-Robot Interaction in Surgical Environment, SICE-ICASE, 2006. International Joint Conference, Oct. 18-21, 2006, pp. 1769-1773, IEEE, Bexco, Busan, SK; 5 pages.

(56)                References Cited

OTHER PUBLICATIONS

Prototype of Instrument for Minimally Invasive Surgery with 6-Axis Force Sensing CapabilityU. Seibold, B. Kubler, and G. Hirzinger, Prototype of Instrument for Minimally Invasive Surgery with 6-Axis Force Sensing Capability, Robotics and Automation, 2005. ICRA 2005. Proceedings of the 2005 IEEE International Conference on, Apr. 18-22, 2005, pp. 498-503, IEEE, Barcelona, Spain; 6 pages.
R. Abovitz, Digital surgery the future of medicine and human-robot symbiotic interaction, Industrial Robot: An International Journal, 2001, pp. 401-406, vol. 28, Issue 5, Hollywood, FL, USA; 5 pages.
R. Buckingham, Robotics in surgery a new generation of surgical tools incorporate computer technology and mechanical actuation to give surgeons much finer control than previously possible during some operations, IEE Review, Sep. 1994, pp. 193-196; 4 pages.
R. Khadem; C.C. Yeh; M.Sadeghi-Tehrani; M.R. Bax; J.A. Johnson; J.L. Welch; E.P. Wilkinson; R. Shahidi, Comparative Tracking Error Analysis of Five Different Optical Tracking Systems, Computer Aided Surgery, 2000, pp. 98-107, vol. 5, Stanford, CA, USA; 10 pages.
R. Rohling; P. Munger; J.M. Hollerbach; T. Peter, Comparison of Relative Accuracy Between a Mechanical and an Optical Position Tracker for Image-Guided Neurosurgery, Journal of Image Guided Surgery, 1995, pp. 30-34, vol. 1, No. 1; 4 pages.
R. Taylor, P. Jensen, L. Whitcomb, A. Barnes, R. Kumar, D. Stoianovici, P. Gupta, Z. Wang, E. Dejuan and L. Kavoussi, A Steady-Hand Robotic System for Microsurgical Augementation, MICCA199: the Second International Conference on Medical Image Computing and Computer-Assisted Intervention, Cambridge, England, Sep. 19-22, 1999. MICCA199 Submission #1361999, pp. 1031-1041, Springer-Verlag Berlin Heidelberg; 11 bages.
R.A. Abovitz, Human-Interactive Medical Robotics, Abstract for CAOS 2000, 2000, pp. 71-72; 2 pages.
R.H. Taylor; B.D. Mittelstadt; H.A. Paul; W. Hanson; P. Kazanzides; J.F. Zuhars; B. Williamson; B.L. Musits; E. Glassman; W.L. Bargar, An Image-Directed Robotic System for Precise Orthopaedic Surgery, Robotics and Automation, IEEE Transactions on, Jun. 1994, pp. 261-275, vol. 10, Issue 3, IEEE; 15 pages.
R.H. Taylor; C.B. Cutting; Y.-Y. Kim; A.D. Kalvin; D. Larose; B.Haddad; D. Khoramabadi; M. Noz; R. Olyha; N. Bruun; D. Grimm, A Model-Based Optimal Planning and Execution System with Active Sensing and Passive Manipulation for Augmentation of Human Precision in Computer-Integrated Surgery, Experimental Robotics II, The 2nd International Symposium, Lecture Notes in Control and Information Sciences, pp. 177-195, vol. 190, Springer Berlin Heidelberg, Toulouse, FR, Jun. 25-27, 1991; 19 pages.
R.H. Taylor; H. A. Paul; B.D. Mittelstadt; W. Hanson; P. Kazanzides; J. Zuhars; E. Glassman; B.L. Musits; B. Williamson; W.L. Bargar, An Image-directed Robotic System for Hip Replacement Surgery, Oct. 1990, pp. 111-116, vol. 8, No. 5; 7 pages.
R.O. Buckingham, Safe Active Robotic Devices for Surgery, Systems, Man and Cybernetics, 1993. 'Systems Engineering in the Service of Humans', Conference Proceedings., International Conference on, Oct. 17-20, 1993, pp. 355-358, vol. 5, IEEE, Le Tougeut; 4 pages.
R.V. O'toole, III; B. Jaramaz; A.M. Digioia, III; C.D. Visnic; R.H. Reid, Biomechanics for Preoperative Planning and Surgical Simulations in Orthopaedics, Computers in Biology and Medicine, Mar. 1995, pp. 183-191, vol. 25, Issue 2; 8 pages.
Re Ellis; CY Tso; JF Rudan; MM Harrison, A surgical planning and guidance system for high tibial osteotomy, Computer Aided Surgery, Apr. 16, 1999, 264-274, vol. 4, Wiley-Liss, Inc.; 11 pages.
S. Haßfeld; C. Burghart; I. Bertovic; J. Raczkowsky; H. Wörn; U. Rembold; J. Mühling, Intraoperative Navigation Techniques Accuracy Tests and Clinical Report, In: Computer Assisted Radiology and Surgery (CARS'98), Tokyo, Jun. 1998, pp. 670-675, Elseview Science B.V.; 6 pages.
S. J. Harris; W. J. Lin; K. L. Fan; R. D. Hibberd; J. Cobb; R. Middleton; B. L. Davies, Experiences with Robotic Systems for Knee Surgery, CVRMed-MRCAS'97, Lecture Notes in Computer Science, 1997, pp. 757-766, vol. 1205, Springer Berlin Heidelberg, London, UK; 10 pages.
S. Lavallee, P. Sautot, J. Troccaz P. Cinquin and P. Merloz, Computer Assisted Spine Surgery a technique for accurate transpedicular screw fixation using CT data and a 3-D optical localizer, Journal of Image Guided Surgery, 1995, pp. 65-73; 9 pages.
S.C. Ho; R.D. Hibberd; B.L. Davies, Robot Assisted Knee Surgery, IEEE Engineering in Medicine and Biology, May/Jun. 1995, pp. 292-300, vol. 14, No. 3; 9 pages.
S.C. Ho; R.D. Hibberd; J. Cobb; B.L. Davies, Force Control for Robotic Surgery, ICAR '95, 1995, pp. 21-32, London, UK; 12 pages.
S.J. Harris; M. Jakopec; J. Cobb; B.L. Davies, Intra-operative Application of a Robotic Knee Surgery System, Medical Image Computing and Computer-Assisted Intervention—MICCAI'99, 1999, pp. 1116-1124, vol. 1679, Springer-Verlag Berlin Heidelberg; 9 pages.
S.L. Delp; S. D. Stulberg; B. Davies; F. Picard; F. Leitner, Computer Assisted Knee Replacement, Clinical Orthopaedics, Sep. 1998, pp. 49-56, vol. 354, Lippincott-Raven Publishers; 8 pages.
Stryker SA, precisioN Knee Navigation Operative Technique for precision Knee Software, Literature No. MTX9100001117, Oct. 2007, Stryker; 40 pages.
T. J. Levison, J. E. Moody, B. Jaramaz, C. Nikou, A. M. Digioia, Surgical Navigation for THR A Report on Clinical Trial Utilizing HipNav, MICCAI 2000, LNCS 1935, pp. 1185-1187, 2000, Springer-Verlag Berlin Heidelberg; 3 pages.
T. Schmidt; W. Hentschel, EasyGuide Neuro, A New System for Image-Guided Planning, Simulation and Navigation in Neurosurgery, Biomedical Engineering, vol. 40, Supplement 1, 1995, pp. 233-234, Hamburg, DE; 2 pages.
T. Wang; M. Fadda; M. Marcacci; S. Martelli; P. Dario; A. Visani, A robotized surgeon assistant, Intelligent Robots and Systems '94. 'Advanced Robotic Systems and the Real World', IROS '94. Proceedings of the IEEE/RSJ/GI International Conference on, Sep. 12-16, 1994, pp. 862-869, vol. 2, IEEE, Munich, Germany, 8 pages.
T.C. Kienzle, III, S.D. Stulberg, M. Peshkin, A. Quaid, J. Lea, A. Goswami, C.H. Wu, Total Knee Replacement Computer-assisted surgical system uses a calibrated robot, Engineering in Medicine and Biology, May 1995, pp. 301-306, vol. 14, Issue 3, IEEE; 35 pages.
T.C. Kienzle, III; S.D. Stulberg; M. Peshkin; A. Quaid; C.-H. Wu, An Integrated CAD-Robotics System for Total Knee Replacement Surgery, Systems, Man and Cybernetics, 1992., IEEE International Conference on, Oct. 18-21, 1992, pp. 1609-1614, vol. 2, IEEE, Chicago, IL, USA; 6 pages.
U. Rembold and C.R. Burghart, Surgical Robotics: An Introduction, Journal of Intelligent and Robotic Systems vol. 30, No. 1, pp. 1-28, 2001, Kluwer Academic Publishers; 28 pages.
U. Spetzger; G. Laborde; J.M. Gilsbach, Frameless Neuronavigation in Modern Neurosurgery, Minimally Invasive Neurosurgery, Dec. 1995, pp. 163-166, vol. 38; 4 pages.
W. Siebert; S. Mai; R. Kober; P.F. Heeckt, Technique and first clinical results of robot-assisted total knee replacement, The Knee, Sep. 2002, pp. 173-180, vol. 9, Issue 3, Elsevier B.V.; 8 pages.
W.L. Bargar; A. Bauer; M. Borner, Primary and Revision Total Hip Replacement Using the Robodoc System, Clinical Orthopaedics and Related Research, Sep. 1998, pp. 82-91, No. 354; 10 pages.
Y. Koseki; K. Chinzei; N. Koyachi; T. Arai, Robotic assist for MR-guided surgery using leverage and parallelepiped mechanism, Medical Image Computing and Computer-Assisted Intervention—MICCAI 2000, Lecture Notes in Computer Science, 2000, pp. 940-948, vol. 1935, Springer Berlin Heidelberg; 9 pages.
Y. Louhisalmi; T. Leinonen, Development of a Robotic Surgical Assistant, 1994, pp. 1043-1044, IEEE, Linnanmaa, Oulu, FI; 2 pages.

* cited by examiner 28,29

"Adjust Camera to Position Shown"

28,29

"Adjust Camera to Position Shown"

"Place Patient in Above Window and Align the Top Left Corner of the Operating Table in the Bracket as Shown"

"Place Trackers on Femur and Tibia As Shown with Base of Femur Tracker Placed One Palm Width Above Patella and Base of Tibia Tracker Placed One Palm Width Below Tibial Tubercle"

28,29

113

"Place Trackers on Femur and Tibia As Shown with Base of Femur Tracker Placed One Palm Width Above Patella and Base of Tibia Tracker Placed One Palm Width Below Tibial Tubercle"

28,29,59

SYSTEM AND METHOD FOR ARRANGING OBJECTS IN AN OPERATING ROOM IN PREPARATION FOR SURGICAL PROCEDURES

RELATED APPLICATIONS

This application is continuation of U.S. nonprovisional patent application Ser. No. 16/447,422, filed on Jun. 20, 2019, which is a divisional of U.S. nonprovisional patent application Ser. No. 15/591,343, filed on May 10, 2017, now U.S. Pat. No. 10,410,746, which claims the benefit of U.S. nonprovisional patent application Ser. No. 14/203,663, filed on Mar. 11, 2014, now U.S. Pat. No. 9,652,591, which claims benefit of U.S. Provisional Patent Application Ser. No. 61/779,725, filed on Mar. 13, 2013, the entire contents of each of the aforementioned applications being hereby incorporated by reference.

TECHNICAL FIELD

The present disclosure relates generally to a system and method for arranging objects in an operating room in preparation for a surgical procedure.

BACKGROUND

Before starting a surgical procedure, many objects need to be properly arranged in the operating room. Such objects include equipment, the patient, surgical personnel, instruments, and the like. Proper arrangement of these objects in the operating room, before the procedure begins, helps to ensure that the surgical procedure proceeds without unnecessary delays. Traditionally, objects are arranged according to written protocols that may include operating room layouts and written instructions associated with the particular procedure being performed.

In some surgical procedures, navigation equipment such as sensing devices (e.g., tracking cameras, magnetic field sensors, etc.) and tracking devices require arrangement before the procedure starts. Navigation systems employ such navigation equipment to assist users in locating objects. For instance, navigation systems assist surgeons in precisely placing surgical instruments relative to a patient's anatomy. Surgeries in which navigation systems are used include neurosurgery and orthopedic surgery. Typically, the instrument and the anatomy are tracked together with their relative movement shown on a display.

Navigation systems may employ light signals, sound waves, magnetic fields, RF signals, etc. in order to track the position and/or orientation of objects. Tracking devices are attached to the objects being tracked. A localizer, which includes the sensing devices, cooperates with the tracking devices to determine a position of the tracking devices, and ultimately to determine a position and/or orientation of the objects. The navigation system monitors movement of the objects via the tracking devices.

Many navigation systems rely on an unobstructed line-of-sight between the tracking devices and sensing devices. When the line-of-sight is obstructed, signals being transmitted from the tracking devices are not received by the sensing devices. As a result, errors can occur. Typically, in this situation, navigation is discontinued and error messages are conveyed to the user until the line-of-sight returns or the system is reset. This can cause delays to surgical procedures. In other types of navigation systems, such as those that rely on sensing magnetic fields, errors can also occur with respect to placement of the tracking and/or sensing devices. For example, metal in the magnetic field can cause inaccuracies in determining the position and/orientation of objects being tracked.

As a result, there is a need in the art for systems and methods to assist in arranging the tracking devices and/or sensing devices to help reduce possible errors. There is also a need in the art to use such systems and methods to arrange other objects in the operating room based on the particular procedure to be performed.

SUMMARY

In a first aspect, a system is provided for guiding arrangement of a robotic system in an operating room, the system comprising: one or more controllers configured to: evaluate surgical procedure information; and determine a desired placement of the robotic system in the operating room based on evaluation of the surgical procedure information; a localizer configured to determine a current placement of the robotic system in the operating room; and a display disposed in the operating room and being coupled to the one or more controllers, the display being configured to display visual representations of the current placement and the desired placement of the robotic system to guide a user on manual placement of the robotic system in the operating room.

In a second aspect, a method is provided for guiding arrangement of a robotic system in an operating room using a localizer, one or more controllers, and a display coupled to the one or more controllers and being disposed in the operating room, the method comprising: evaluating surgical procedure information with the one or more controllers; determining, with the one or more controllers, a desired placement of the robotic system in the operating room based on evaluating the surgical procedure information; determining, with the localizer, a current placement of the robotic system in the operating room; and guiding a user on manual placement of the robotic system in the operating room by displaying, on the display, visual representations of the current placement and the desired placement of the robotic system.

In a third aspect, a non-transitory computer-readable medium is provided that is usable with a system comprising one or more controllers, a localizer, and a display, the non-transitory computer-readable medium having stored thereon instructions that implement a software module for guiding arrangement of a robotic system in an operating room, the instructions, when executed by the one or more controllers, are configured to: evaluate surgical procedure information; determine a desired placement of the robotic system in the operating room based on evaluation of the surgical procedure information; obtain, from the localizer, a current placement of the robotic system in the operating room; and instruct the display to display visual representations of the current placement and the desired placement of the robotic system to guide a user on manual placement of the robotic system in the operating room.

One advantage of these embodiments is to facilitate arranging objects in the operating room in an efficient manner and based on the particular procedure to be performed so that the objects are placed in desired locations for that particular procedure.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

Figure 1:
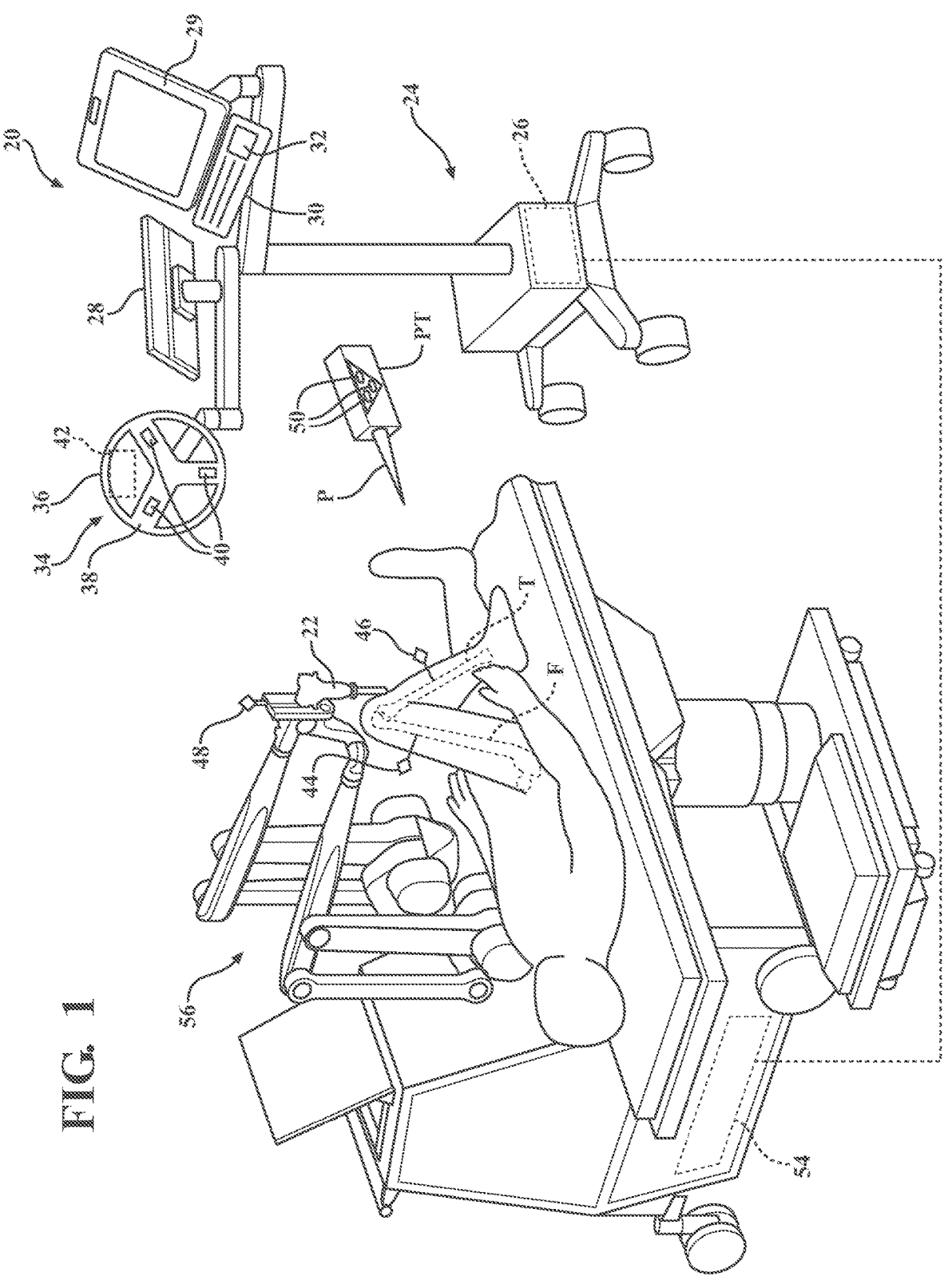
FIG. 1 is a perspective view of a guidance station being used in conjunction with a robotic manipulator.
Figure 2:
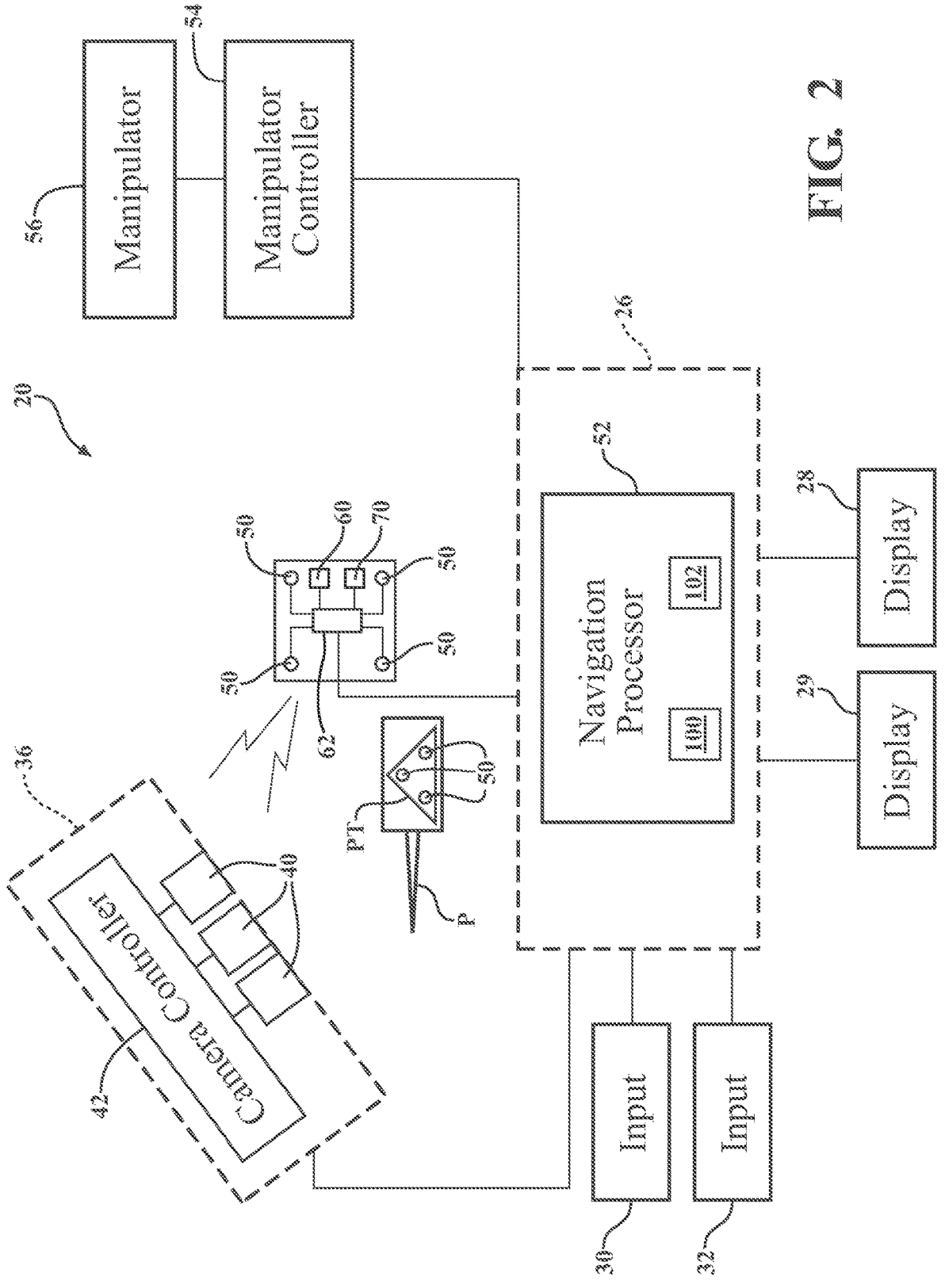
FIG. 2 is a schematic view of the guidance station, tracking devices, pointer, and machining station.

Systems and methods are disclosed for arranging objects in an operating room. Referring to FIGS. 1 and 2, in one embodiment, the system includes a guidance station 20 and tracking elements associated with various objects. The tracking elements are capable of communicating with the guidance station 20 to track the objects. Procedure information is provided to the guidance station 20. The procedure information may come from a pre-operative surgical plan and/or be provided intra-operatively. Based on the procedure information (e.g., identification of anatomy being treated, type of procedure—such as hip replacement surgery or total or partial knee replacement surgery, implant types/sizes, patient information, surgeon preferences, etc.), the guidance station 20 performs the steps of determining a desired placement of the objects and guiding surgical personnel to place the objects according to the desired placement. One advantage of this system and method is to reduce setup time in the operating room and improve the efficiency of surgeries.

In FIG. 1, the guidance station 20 is shown in an operating room of a medical facility. The guidance station 20 is set up to track movement of the various objects in the operating room. Such objects include, for example, a surgical instrument 22, a femur F, and a tibia T. The guidance station 20 tracks these objects for purposes of displaying their relative positions and orientations to the surgeon and, in some cases, for purposes of controlling or constraining movement of the surgical instrument 22 relative to a predefined path or anatomical boundary. The guidance station 20 also assists in arranging these objects and other objects in the operating room prior to the start of a surgical procedure and/or intra-operatively, as will be discussed further below.

The guidance station 20 includes a computer cart assembly 24 that houses a navigation computer 26, or other type of control unit. A navigation interface is in operative communication with the navigation computer 26. The navigation interface includes a first display 28 adapted to be situated outside of the sterile field and a second display 29 adapted to be situated inside the sterile field. The displays 28, 29 are adjustably mounted to the computer cart assembly 24. First and second input devices 30, 32 such as a keyboard and mouse can be used to input information into the navigation computer 26 or otherwise select/control certain aspects of the navigation computer 26. Other input devices are contemplated including a touch screen (not shown) or voice-activation.

A localizer 34 communicates with the navigation computer 26. In the embodiment shown, the localizer 34 is an optical localizer and includes a camera unit 36 (also referred to as a sensing device). The camera unit 36 has an outer casing 38 that houses one or more optical position sensors 40. In some embodiments at least two optical sensors 40 are employed, preferably three or more. The optical sensors 40 may be three separate charge-coupled devices (CCD). In one embodiment three, one-dimensional CCDs are employed. It should be appreciated that in other embodiments, separate camera units, each with a separate CCD, or two or more CCDs, could also be arranged around the operating room. The CCDs detect infrared (IR) signals.

Camera unit 36 is mounted on an adjustable arm to position the optical sensors 40 with a field of view of the below discussed trackers that, ideally, is free from obstructions. The adjustable arm allows adjustment of the camera unit 36 in at least one degree of freedom and, in some embodiments, in two or more degrees of freedom.

The camera unit 36 includes a camera controller 42 in communication with the optical sensors 40 to receive signals from the optical sensors 40. The camera controller 42 communicates with the navigation computer 26 through either a wired or wireless connection (not shown). One such connection may be an IEEE 1394 interface, which is a serial bus interface standard for high-speed communications and isochronous real-time data transfer. The connection could also use a company specific protocol. In other embodiments, the optical sensors 40 communicate directly with the navigation computer 26.

Position and orientation signals and/or data are transmitted to the navigation computer 26 for purposes of tracking the objects. The displays 28, 29 and camera unit 36 may be like those described in U.S. Pat. No. 7,725,162 to Malackowski, et al. issued on May 25, 2010, entitled "Surgery System", hereby incorporated by reference.

The navigation computer 26 can be a personal computer or laptop computer. Navigation computer 26 has the displays 28, 29, central processing unit (CPU) and/or other processors, memory (not shown), and storage (not shown). The navigation computer 26 is loaded with software as described below. The software converts the signals/data received from the camera unit 36 into data representative of the position and orientation of the objects being tracked.

Guidance station 20 communicates with a plurality of tracking devices 44, 46, 48, also referred to herein as trackers. In the illustrated embodiment, one tracker 44 is firmly affixed to the femur F of the patient and another tracker 46 is firmly affixed to the tibia T of the patient. Trackers 44, 46 are firmly affixed to sections of bone. Trackers 44, 46 may be attached to the femur F and tibia T in the manner shown in U.S. Pat. No. 7,725,162, hereby incorporated by reference. Trackers 44, 46 could also be mounted like those shown in U.S. Provisional Patent Application No. 61/753,219, filed on Jan. 16, 2013, entitled, "Tracking Devices and Navigation Systems and Methods for Use Thereof", hereby incorporated by reference herein. In additional embodiments, a tracker is attached to the patella (not shown) to track a position and orientation of the patella. In yet further embodiments, the trackers 44, 46 could be mounted to other tissue types or parts of the anatomy.

An instrument tracker 48 is rigidly attached to the surgical instrument 22. The instrument tracker 48 may be integrated into the surgical instrument 22 during manufacture or may be separately mounted to the surgical instrument 22 in preparation for the surgical procedure. The working end of the surgical instrument 22, which is being tracked by virtue of the instrument tracker 48, may be a rotating bur, electrical ablation device, or the like.

The trackers 44, 46, 48 can be battery powered with an internal battery or may have leads to receive power through the navigation computer 26, which, like the camera unit 36, preferably receives external power.

In the embodiment shown, the surgical instrument 22 is an end effector of a machining station 56. Such an arrangement is shown in U.S. Provisional Patent Application No. 61/679, 258, entitled, "Surgical Manipulator Capable of Controlling a Surgical Instrument in either a Semi-Autonomous Mode or a Manual, Boundary Constrained Mode", the disclosure of which is hereby incorporated by reference. A separate tracker (not shown) may be attached to a mobile cart 57 of the machining station 56 to track movement of the cart 57. Alternatively, through joint position sensors (not shown) such as position encoders, the guidance station 20 is able to determine a position of the cart 57 based on the position and orientation of the instrument tracker 48 and owing to the rigid connection of the instrument tracker 48 relative to the machining station 56.

The optical sensors 40 of the localizer 34 receive light signals from the trackers 44, 46, 48. In the illustrated embodiment, the trackers 44, 46, 48 are active trackers. In this embodiment, each tracker 44, 46, 48 has at least three active tracking elements or markers for transmitting light signals to the optical sensors 40. The active markers can be, for example, light emitting diodes or LEDs 50 transmitting light, such as infrared light. The optical sensors 40 preferably have sampling rates of 100 Hz or more, more preferably 300 Hz or more, and most preferably 500 Hz or more. In some embodiments, the optical sensors 40 have sampling rates of 8000 Hz. The sampling rate is the rate at which the optical sensors 40 receive light signals from sequentially fired LEDs 50. In some embodiments, the light signals from the LEDs 50 are fired at different rates for each tracker 44, 46, 48.

Referring to FIG. 2, each of the LEDs 50 are connected to a tracker controller 62 located in a housing (not shown) of the associated tracker 44, 46, 48 that transmits/receives data to/from the navigation computer 26. In one embodiment, the tracker controllers 62 transmit data on the order of several Megabytes/second through wired connections with the navigation computer 26. In other embodiments, a wireless connection may be used. In these embodiments, the navigation computer 26 has a transceiver (not shown) to receive the data from the tracker controller 62.

In other embodiments, the trackers 44, 46, 48 may have passive markers (not shown), such as reflectors that reflect light emitted from the camera unit 36. The reflected light is then received by the optical sensors 40. Active and passive tracking elements are well known in the art.

The navigation computer 26 includes a navigation processor 52. The camera unit 36 receives optical signals from the LEDs 50 of the trackers 44, 46, 48 and outputs to the processor 52 signals relating to the position of the LEDs 50 of the trackers 44, 46, 48 relative to the localizer 34. Based on the received optical signals, navigation processor 52 generates data indicating the relative positions and orientations of the trackers 44, 46, 48 relative to the localizer 34. In some embodiments, the trackers 44, 46, 48 also include a gyroscope sensor 60 and accelerometer 70, such as the trackers shown in U.S. Provisional Patent Application No. 61/753,219, filed on Jan. 16, 2013, entitled, "Tracking Devices and Navigation Systems and Methods for Use Thereof", hereby incorporated by reference.

It should be understood that the navigation processor 52 could include one or more processors to control operation of the navigation computer 26. The processors can be any type of microprocessor or multi-processor system. The term processor is not intended to limit the scope of the invention to a single processor.

Based on the positions of the LEDs 50 and previously loaded data relating to the patient's anatomy and the surgical instrument 22, navigation processor 52 determines the position and orientation of the surgical instrument 22 relative to the tissue (e.g., femur F and tibia T) against which the working end is to be applied. The previously loaded data includes data associated with pre-operative images, including MRI images, CT scans, etc. taken before the surgical procedure. The previously loaded data also includes geometric relationships between the working end of the surgical instrument 22 and the LEDs 50 on instrument tracker 48. Using well known navigation techniques for registration and coordinate system transformation, the patient's anatomy and the working end of the surgical instrument 22 can be registered into a coordinate reference frame of the localizer 34 so that the working end and the anatomy can be tracked together using the LEDs 50.

In some embodiments, navigation processor 52 forwards position and/or orientation data to a manipulator controller 54. The manipulator controller 54 can then use the data to control the machining station 56 as described in U.S. Provisional Patent Application No. 61/679,258, entitled, "Surgical Manipulator Capable of Controlling a Surgical Instrument in either a Semi-Autonomous Mode or a Manual, Boundary Constrained Mode," the disclosure of which is hereby incorporated by reference.

The navigation processor 52 also generates image signals that indicate the relative position of the surgical instrument working end to the surgical site. These image signals are applied to the displays 28, 29. Displays 28, 29, based on these signals, generate images that allow the surgeon and surgical personnel to view the relative position of the surgical instrument working end to the surgical site. The displays, 28, 29, as discussed above, may include a touch screen or other input/output device that allows entry of commands.

Referring to FIG. 2, a localization engine 100 is a software module that can be considered part of the guidance station 20. Components of the localization engine 100 run on navigation processor 52. In some versions of the invention, the localization engine 100 may run on the manipulator controller 54.

Localization engine 100 receives as inputs the optically-based signals from the camera controller 42 and, in some embodiments, the non-optically based signals from the tracker controller 62. Based on these signals, localization engine 100 determines the pose of the trackers 44, 46, 48 in the localizer coordinate system. The localization engine 100 forwards the signals representative of the poses of trackers 44, 46, 48 to a coordinate transformer 102. Coordinate transformer 102 is a navigation system software module that runs on navigation processor 52. Coordinate transformer 102 references the data that defines the relationship between the pre-operative images of the patient and the patient trackers 44, 46. Coordinate transformer 102 also stores the data indicating the pose of the working end of the surgical instrument relative to the instrument tracker 48.

The coordinate transformer 102 then generates data indicating the position and orientation of the working end of the surgical instrument 22 relative to the tissue (e.g., bone) against which the instrument working end is applied. Image signals representative of these data are forwarded to displays 28, 29 enabling the surgeon and surgical personnel to view this information. To avoid interruption of this data, the line-of-sight between the trackers 44, 46, 48 and the sensors 40 is to be maintained. If there are obstructions to the line-of-sight, then errors may occur.

The guidance station 20 is configured to assist with the pre-surgery and/or intra-operative placement of objects, such as the trackers 44, 46, 48, used in the operating room during a surgical procedure. The guidance station 20 provides instructions on the arrangement of the objects to facilitate procedural efficiency and to reduce possible obstructions to navigation during the surgical procedure. Other objects that may be arranged according to instructions from the guidance station 20 may include, but are not limited to, the patient, the machining station 56, surgical personnel, the camera unit 36, other instruments, equipment, or stations, and the like. The instructions provided by the guidance station 20 may be based on procedure information such as the type of procedure being performed, preferences of the surgeon performing the procedure, implant types/sizes, patient information, and other factors.

Figures 3, 4:
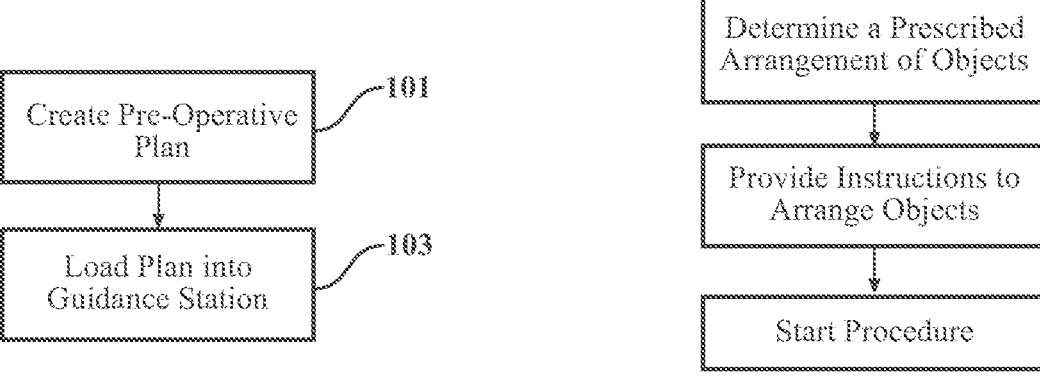
FIG. 3 is a flow diagram of steps carried out to create a pre-operative plan and load the pre-operative plan into the system.
FIG. 4 is a flow diagram of steps carried out by the guidance station.

Referring to FIG. 3, in the embodiment shown, the instructions from the guidance station 20 are provided based on the pre-operative plan. The pre-operative plan is created in step 101. Pre-operative plans are prescribed by surgeons for each patient and describe in detail the type of procedure being performed, the target anatomy that is being treated, the types, sizes, and/or shapes of implants (if any) that are being implanted, surgeon preferences, and other information.

Creation of the pre-operative plan includes several steps. First, the patient is diagnosed to determine the appropriate treatment for the patient. Next, the surgeon prescribes the treatment. In the embodiment shown, the treatment is a total knee replacement. The surgeon's prescription includes the imaging of the patient's bones, i.e., the femur and tibia using MM, CT scan, etc. Once imaging of the bones is complete, the images are used to prepare or select an appropriate design of a total knee implant. The design can also be based on a kinematic study of the patient performed in the operating room (OR) immediately prior to the surgery.

The design includes the type of implant, the size/shape of the implant, and the location on the bones to which the implant is to be fixed (which includes identifying the tissue to be removed to receive the implant). This information may be stored in electronic form in a computer readable format such as a text file, image file, or the like. The design may be prepared or selected by the surgeon or by a third party. Once the design of the knee implant is determined, the surgeon reviews the design, and if acceptable, approves the design and the surgical procedure is scheduled. Once the surgical procedure is scheduled, the operating room is prepared for the surgery, which includes arranging the objects based on the pre-operative plan.

In other embodiments, the objects are arranged based on procedure information determined at the time of the surgery, i.e., not pre-operatively.

The pre-operative plan is stored on the guidance station 20 in step 103. The pre-operative plan may be stored in the navigation computer 26 using a wired or wireless internet connection to the navigation computer 26, by flash memory device, or the like. In some cases, the surgeon or his or her designee transfers the encrypted pre-operative plan (including design information) to the guidance station 20, via hospital or surgical center secure local area network (Ethernet), secure USB flash drive, or secure wireless (WiFi) connection. In some embodiments, the pre-operative plan is created using the guidance station 20.

Referring to FIG. 4, once the procedure information (e.g., information from pre-operative plan) is stored in the navigation computer 26, an OR Setup module 109 (see FIG. 2) can be used to begin setting up the objects in the operating room. The OR Setup module 109 is a software module that runs on navigation computer 26. The surgical personnel can operate the OR Setup module 109 using the user interface and displays 28, 29 of the guidance station 20. When using the OR Setup module 109, the surgical personnel first load the procedure information (e.g., pre-operative plan) into the OR Setup module 109. When loaded, certain information is made available to the OR Setup module 109.

The OR Setup module 109 determines a prescribed arrangement of objects based on the procedure information in step 104. The prescribed arrangement of objects can be determined by looking for certain information loaded into the OR Setup module 109 and matching the information to one of a plurality of prescribed arrangements listed in a look-up table. The look-up table is stored on the navigation computer 26. For instance, the information loaded may identify the type of procedure as "TOTAL KNEE—LEFT". The OR Setup module 109 is programmed to select a prescribed arrangement of objects based on this type of procedure by finding in the look-up table the specific arrangement associated with "TOTAL KNEE—LEFT".

Figure 6:
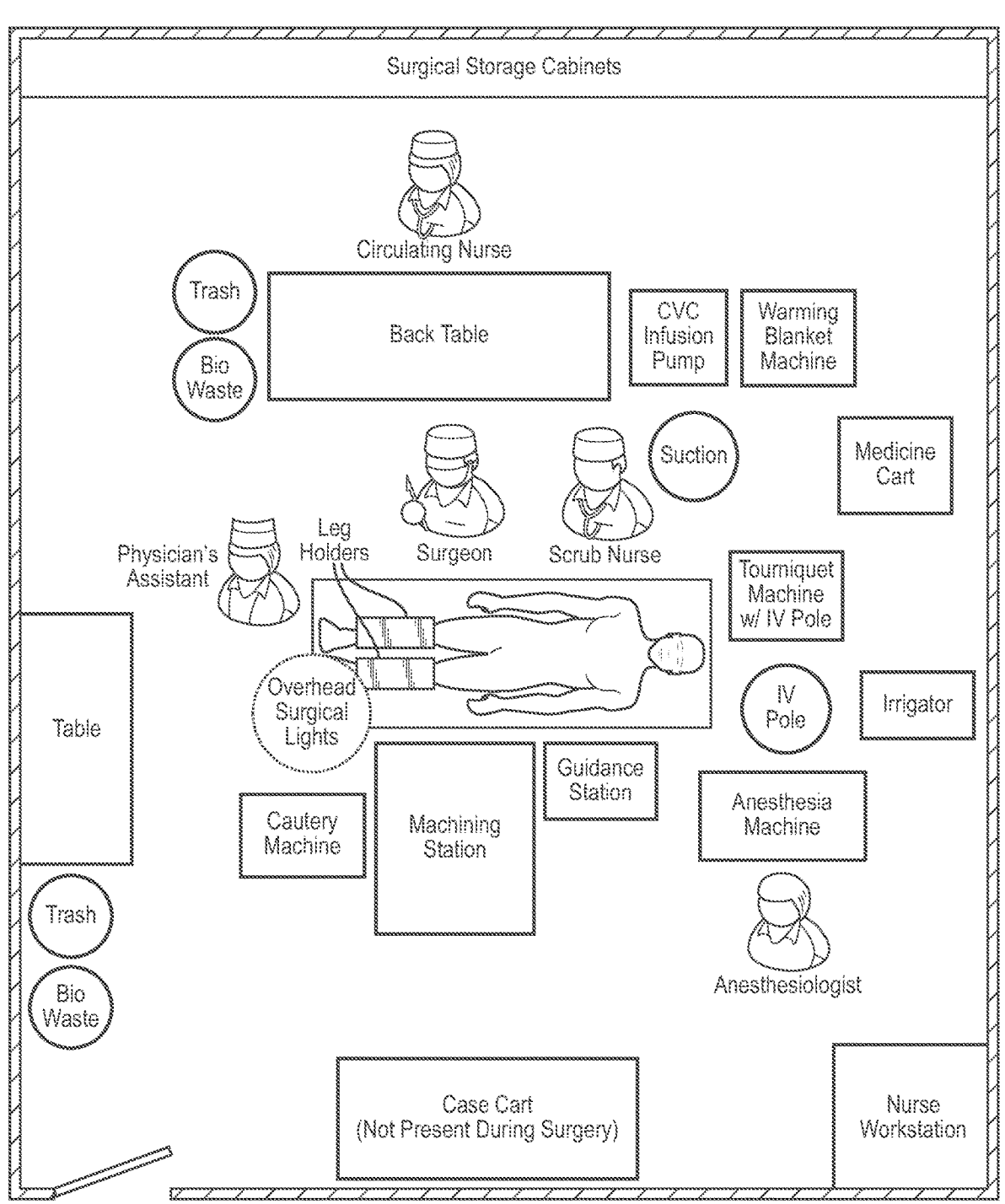
FIG. 6 is an overhead view of a sample right-handed operating room layout.
Figure 7:
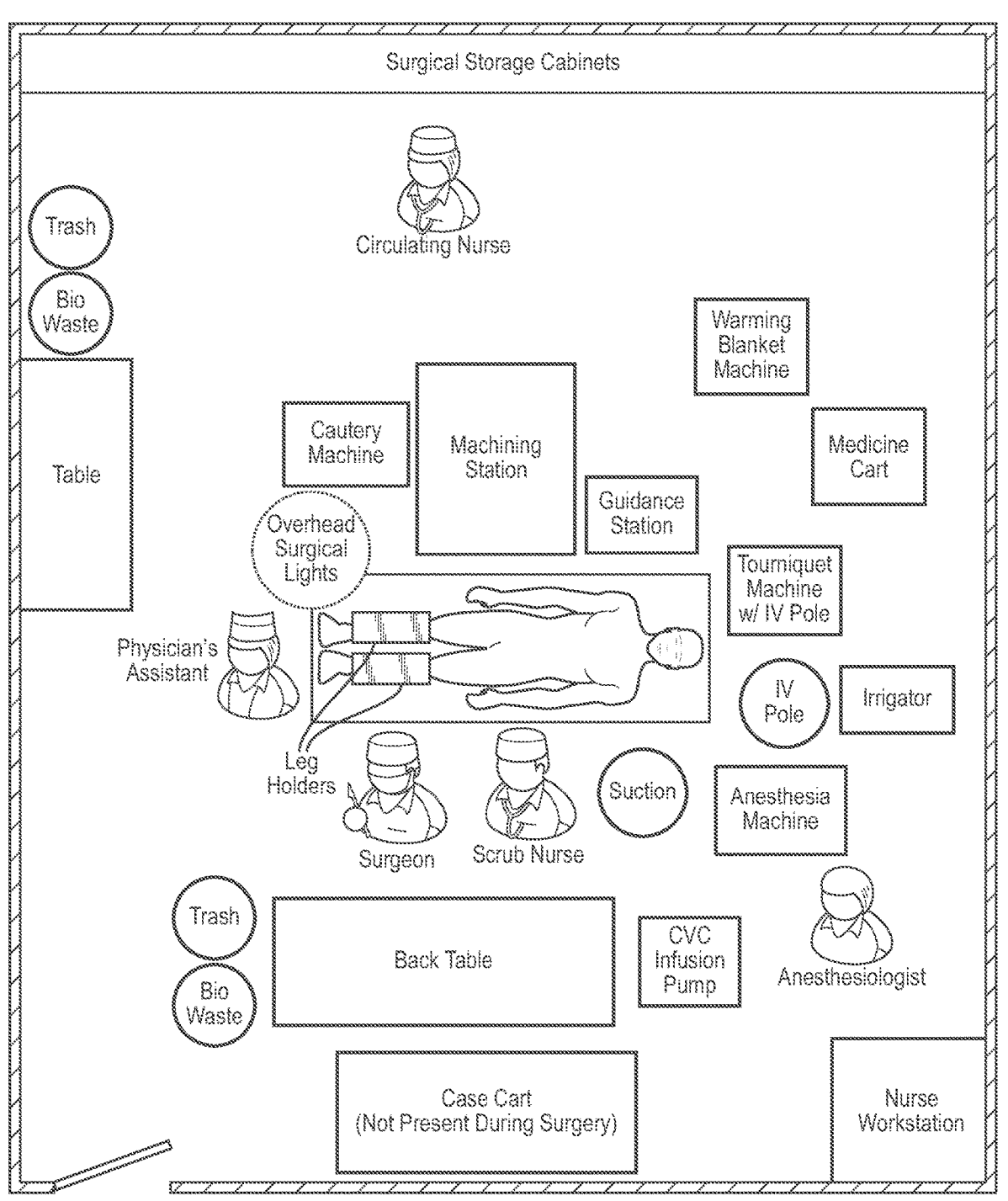
FIG. 7 is an overhead view of a sample left-handed operating room layout.

Prescribed arrangements include overhead layouts such as those shown in FIGS. 6 and 7. These overhead layouts may be stored in the navigation computer 26 as image files or other file types. Alternatively, the overhead layouts may be part of the pre-operative plan and/or loaded along with the procedure information into the OR Setup module 109. Different layouts may be associated with different procedure types. Different layouts may also be associated with different surgeon preferences. For example, the layout shown in FIG. 6 is for a right-handed surgeon, while the layout shown in FIG. 7 is for a left-handed surgeon.

Figure 5:
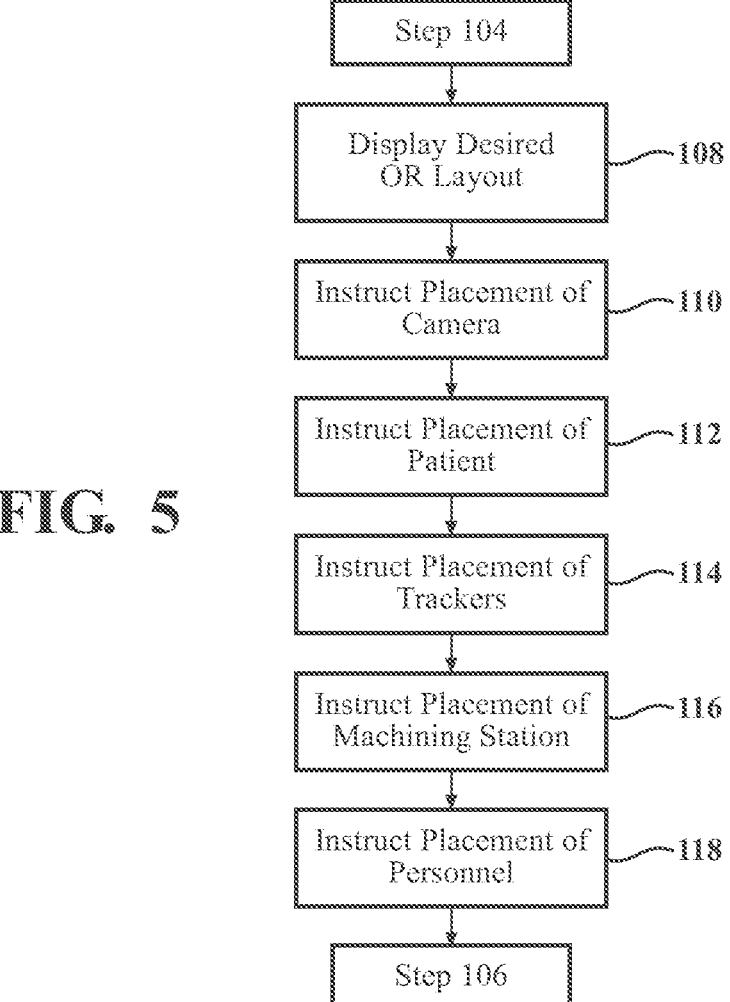
FIG. 5 is a flow diagram of steps carried out by the guidance station to assist in arranging objects in an operating room.

Once the prescribed arrangement is determined, the guidance station 20 provides instructions to arrange the objects accordingly in step 105. Such instructions can be carried out in the order shown in FIG. 5. Other orders of these instructions are also contemplated.

In step 108, the guidance station 20 displays the overhead layout determined by the OR Setup module. The overhead layout is shown on the displays 28, 29. The overhead layout provides the surgical personnel with instructions on the gross placement of the objects including the guidance station 20, the patient and operating table, the machining station 56, the surgeon, nurses, and other objects. As described further below, more precise positioning of trackers 44, 46 and the machining station 56 is also navigationally guided by the guidance station 20.

Now that the overhead layout is shown, the surgical personnel can move the guidance station 20 into its indicated position on the overhead layout. Once in position, the method moves to step 110 which directs placement of the camera unit 36. Transition to step 110 may require input from the surgical personnel, such as selecting "OK" or "DONE" on the displays 28, 29 with an input device to indicate to the OR Setup module 109 that the guidance station 20 is in position.

Figure 5A:
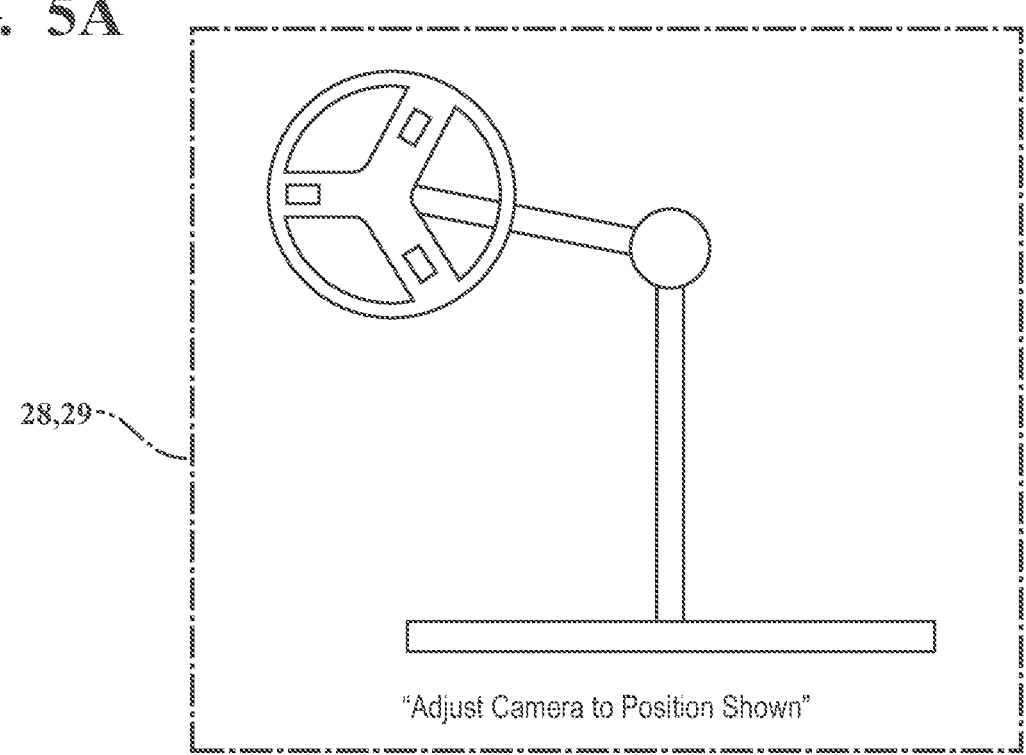
FIG. 5A is an illustration of a screen shot from an OR Setup software module providing instructions on placement of a camera unit.

The camera unit 36 is adjustable about at least one degree of freedom and, in some cases, about two or more degrees of freedom. The guidance station 20, through the OR Setup module 109, instructs the surgical personnel on how to position the camera unit 36. This instruction may include written instructions present on displays 28, 29 to adjust the camera unit 36 to a predetermined height or a predetermine angle relative to ground. Referring to FIG. 5A, the instruction for placement of the camera unit 36 may include visual guidance showing an exemplary setup for the camera unit 36. Once the camera unit 36 is properly placed, transition to step 112 may require input from the surgical personnel, such as selecting "OK" or "DONE" on the displays 28, 29 with an input device to indicate to the OR Setup module 109 that the camera unit 36 is in position.

Figure 5B:
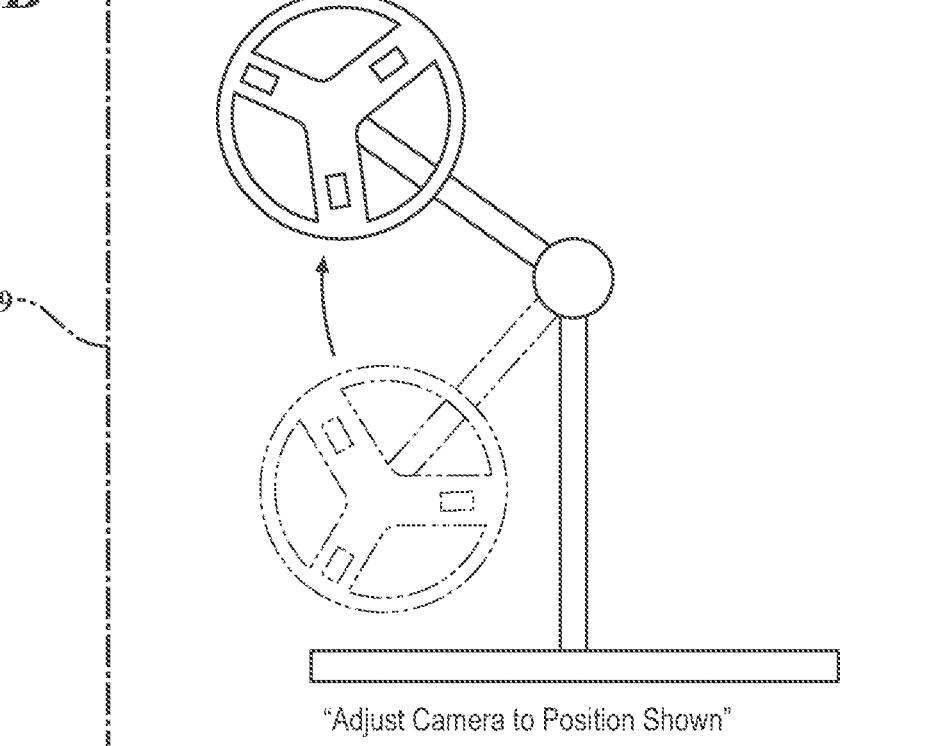
FIG. 5B is an illustration of an alternative screen shot from the OR Setup software module providing instructions on placement of the camera unit.

In some embodiments, joints of the arms for moving the camera unit 36 may have position encoders that can be read by the navigation computer 26 and used to dynamically track movement of the camera unit 36 relative to the ground based on known geometric relationships between the cart assembly 24, ground, adjustment arms, and camera unit 36. In this case, referring to FIG. 5B, visual guidance on the displays 28, 29 can include showing a representation of the current position of the camera unit 36 (shown in hidden lines) relative to a representation of the desired position of the camera unit 36. The representation of the current position dynamically moves on the displays 28, 29 toward or away from the representation of the desired position as the user adjusts a position of the camera unit 36. The OR Setup module 109 can transmit images to the displays 28, 29 showing the direction of required movement to reach the desired position, such as the arrow shown in FIG. 5B. Once the current position of the camera unit 36 is within a predefined tolerance of the desired position, the OR Setup module 109 indicates that the desired position has been reached and moves to Step 112.

The patient is brought into the operating room on the operating table in step 112. The patient, in the case of a total knee replacement, is either brought in under anesthesia or anesthesia is administered in the operating room. The surgical staff may also secure the leg of interest in a leg holder, and drape the patient and equipment. One such leg holder is shown in U.S. patent application Ser. No. 13/554,010, entitled, "Multi-position Limb Holder", published as U.S. Patent Application Publication No. 2013/0019883, hereby incorporated by reference.

Instructions on the placement of the patient may include written instructions on the displays 28, 29 regarding positioning of the operating table relative to the guidance station 20. Such instructions may include establishing a desired distance between the computer cart assembly 24 and the operating table or aligning a particular side of the operating table with respect to the camera unit 36. The instruction for placement of the patient may include visual guidance showing an exemplary setup for the patient relative to the camera unit 36.

In some embodiments, a video camera (not shown) is attached to the camera unit 36. The video camera is oriented such that a field of view of the camera unit 36 can be associated with the field of view of the video camera. In other words, the two fields of view may be matched or otherwise correlated such that if an object (e.g., LEDs 50) can be seen in video images streamed from the video camera, the objects are also within the field of view of the camera unit 36. Video images from the video camera can be streamed to the displays 28, 29 during any of the steps in FIG. 5.

Figure 5C:
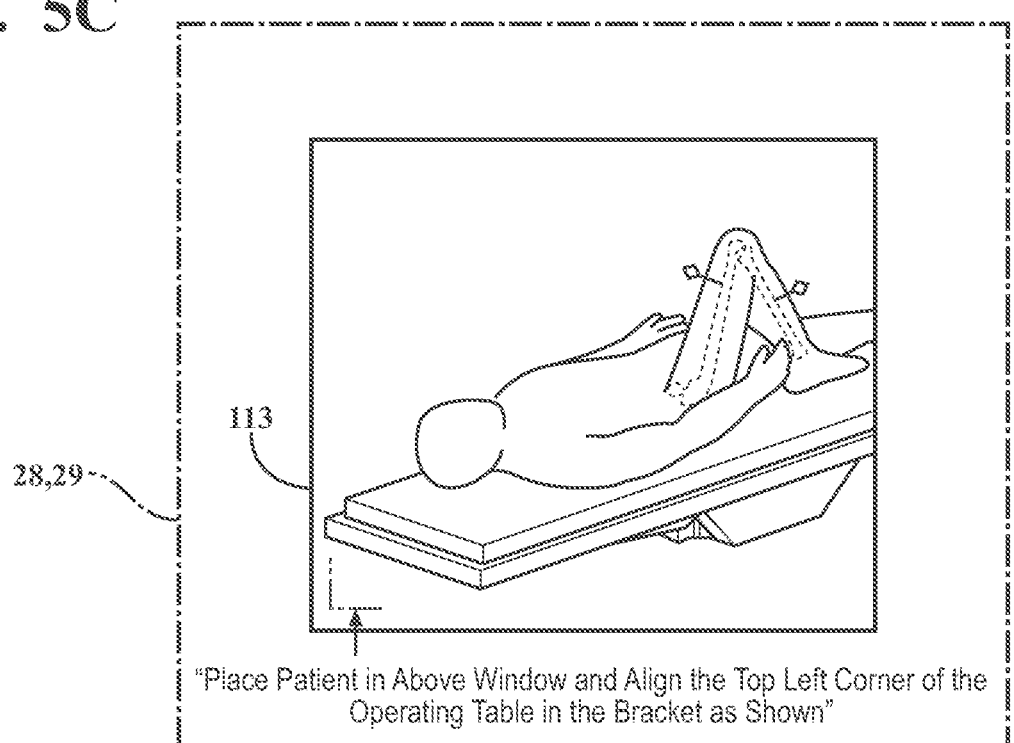
FIG. 5C is an illustration of a screen shot from the OR Setup software module providing instructions on placement of a patient.

In step 112, while the displays 28, 29 show a window 113 with video images streaming from the video camera in the window 113, the instructions provided on the displays 28, 29 may also include written instructions stating to the surgical personnel to place the patient within the window 113. This is illustrated in FIG. 5C. The window 113 may also show where certain edges or sides of the operating table are to be located by overlaying geometric visual aids (such as crosshairs, edge lines, etc.) onto the video images and providing accompanying written instructions. Once the patient is located within the window and the operating table is properly aligned, the patient is positioned according to the pre-operative plan and/or other procedure information. Once the patient is in the proper position, transition to step 114 may require input from the surgical personnel, such as selecting "OK" or "DONE" on the displays 28, 29 with an input device to indicate to the OR Setup module 109 that the patient is in position.

Figure 5D:
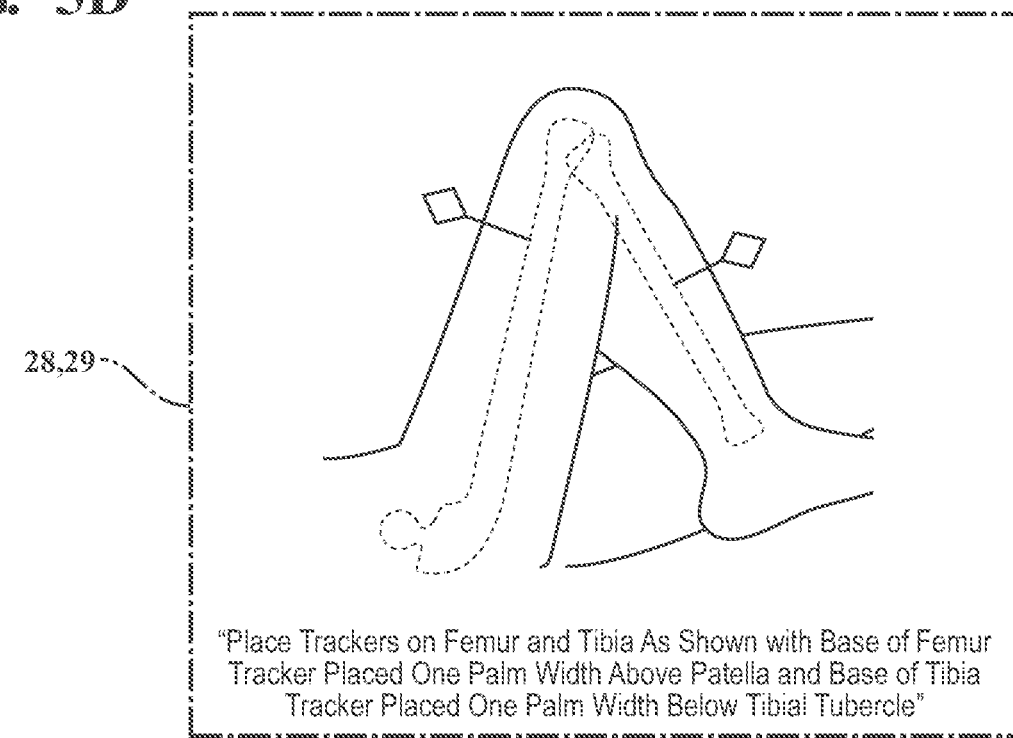
FIG. 5D is an illustration of a screen shot from the OR Setup software module providing instructions on placement of trackers.
Figures 8, 9:
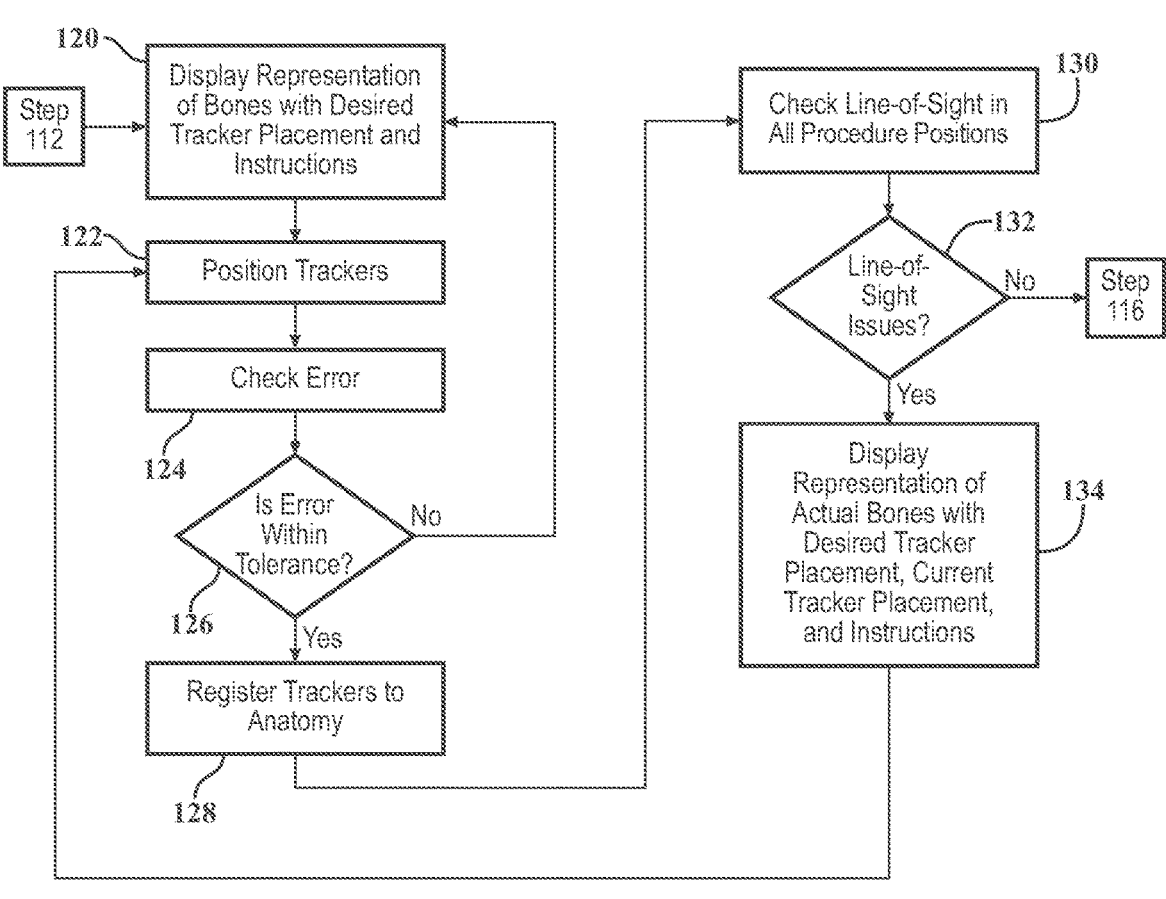
FIG. 8 is a flow diagram of steps carried out to place trackers relative to a patient.
FIG. 9 is a flow diagram of steps carried out to place the machining station.

Tracker placement is performed in step 114. One exemplary embodiment of instructions provided by the guidance station 20 for placing the trackers 44, 46 is shown in FIG. 8. To begin, in step 120, representations of the femur F and tibia T are shown on the displays 28, 29 with desired tracker placement and associated instructions. An example of this is shown in FIG. 5D. Generic bone representations are used to generally show proper placement based on distance from the knee joint, for example, or distances from certain anatomical landmarks associated with the knee joint (e.g., distances from patella, tibial tubercle, etc.). Written instructions on the displays 28, 29 can indicate distances from the anatomical landmarks to each of the trackers 44, 46 (distances may be indicated from landmark to the base of each tracker 44, 46 mounted to bone). A desired distance between trackers 44, 46 (or the bases thereof) may also be numerically and visually depicted on the displays 28, 29. In some embodiments, the instructions on the display 28, 29 include written instructions on the placement of the leg in a leg holder prior to placing the trackers 44, 46 and instructions on securing the leg holder in position. One such leg holder is shown in U.S. patent application Ser. No. 13/554,010, entitled, "Multi-position Limb Holder", published as U.S. Patent Application Publication No. 2013/0019883, hereby incorporated by reference.

Figure 5E:
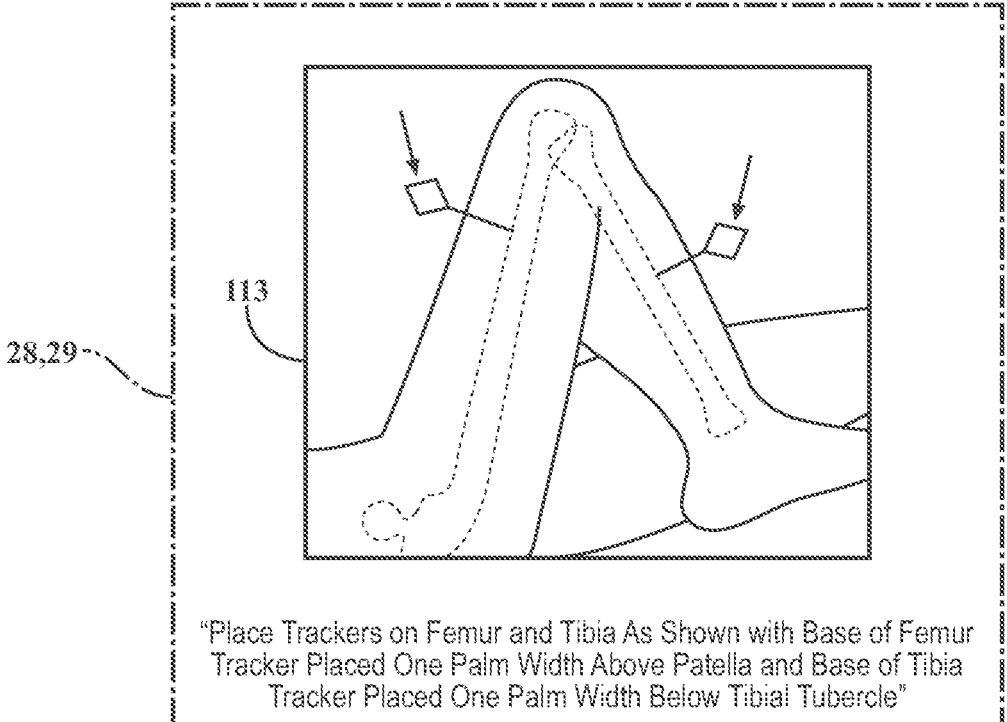
FIG. 5E is an illustration of an alternative screen shot from the OR Setup software module providing instructions on placement of trackers.

The video camera described above may be integrated into a machine vision system of the guidance station 20 with ability to identify the leg of the patient using conventional machine vision technology. Referring to FIG. 5E, once the leg is identified and shown in the window 113 on the displays 28, 29, the guidance station 20 overlays desired positions of the trackers 44, 46 on the displays 28, 29 (shown by arrows), while simultaneously and continuously showing the video images from the video camera, which shows the surgeon and/or surgical personnel placing the trackers 44, 46 (actual trackers not shown in FIG. 5E).

The surgical personnel position the trackers 44, 46 in step 122. This may include placing bone pins and attaching the trackers 44, 46 to the bone pins, or this may include making an incision at the knee joint using manual instruments to gain access to the joint and mounting a bone plate and coupling tracking elements of the trackers 44, 46 to the bone plate such as shown in U.S. Provisional Patent Application No. 61/753,219, filed on Jan. 16, 2013, entitled, "Tracking Devices and Navigation Systems and Methods for Use Thereof", hereby incorporated by reference. Once in position, the camera unit 36 is activated to begin receiving position-related signals from the LEDs 50, of the trackers 44, 46.

In step 124, the navigation computer 26 measures distances between the LEDs 50 on tracker 44 with the LEDs 50 on tracker 46. This provides a basic indication of how far apart the trackers 44, 46 are located on the bones, e.g., femur and tibia. In one embodiment, a shortest distance between the closest two LEDs 50 and a farthest distance between the farthest two LEDs 50 are measured. In step 126 these measure distances are compared to a predetermined range of distances. If both of the shortest and farthest measured distances fall within the range, the method proceeds to step 128. If not, the method goes back to step 120 and the trackers 44, 46 are repositioned according to the instructions in step 120. If the method goes back to step 120, the instructions can additionally include details on whether the trackers 44, 46 were too close together or too far apart—giving the surgical personnel additional guidance on where to position the trackers 44, 46. Repositioning of the trackers 44, 46 may simply require adjustment of the trackers 44, 46 about one or more adjustable degrees of freedom without requiring removal of the base (or bone pins) from the bone. In extreme cases, the trackers 44, 46 will need to be completely removed from the bone and re-mounted.

Once the trackers 44, 46 have been positioned within the predetermined range of distances, then the trackers 44, 46 are registered to the anatomy. Registration of bone surfaces and reference landmarks is well-known in the art using pointers P and will not be described in detail. Registration results in the pre-operative MRI or CT images being associated with positions of the LEDs 50 on the trackers 44, 46. As a result, movement of the femur F and tibia T can be tracked by tracking movement of the LEDs 50.

Once the positions and orientations of the femur F and tibia T are registered to the LEDs 50, the navigation computer 26 can simulate movement of the femur F and tibia T through a range of motion from flexion to extension and in all anticipated positions of the femur and tibia during the surgical procedure. For instance, the procedure may require the knee to be placed in maximum flexion and extension. The navigation processor 52 can simulate where the LEDs 50 will be located at maximum flexion and extension positions of the leg and determine whether the LEDs 50 will be within the field-of-view of each of the sensors 40 in all of these positions since the field-of-view of the sensors 40 is also known to the navigation computer 26. In other words, the navigation computer 26 can simulate movement of the femur F and tibia T during the procedure and detect whether any of the LEDs 50 will be blocked from the field-of-view of any of the sensors 40.

Alternatively, as opposed to running the simulation, the instructions on the displays 28, 29 may require the surgical personnel to actually move the leg through maximum extension and flexion in the leg holder, while the guidance station 20 tracks the LEDs 50 on the trackers 44, 46. Blockage is then identified by determining if at any position of the leg, any of the LEDs 50 is blocked from transmitting signals to the sensors 40.

If blockage is predicted in the simulation or actually detected when moving the leg, then the method proceeds to step 134. In step 134, representations of the actual bones of the patient are shown on the displays 28, 29 along with the current tracker placement and the desired tracker placement (similar to FIG. 5E, but now using navigation position information). Instructions for moving or repositioning the trackers 44, 46 are also displayed on displays 28, 29. In some cases, repositioning may simply require sliding, tilting or rotating a head of one of the trackers 44, 46 using adjustment features of the trackers 44, 46, without requiring complete removal of the trackers 44, 46 from the bone. See, for example, adjustment features of the trackers shown in U.S. Provisional Patent Application No. 61/753,219, filed on Jan. 16, 2013, entitled, "Tracking Devices and Navigation Systems and Methods for Use Thereof", hereby incorporated by reference. In other cases, one or both of the trackers 44, 46 need to be removed from the bones.

Once repositioned, the initial error check in step 124 is performed again. If the error is acceptable, then the trackers 44, 46 are re-registered to the anatomy and the remaining steps continue as before. At step 132, if no blockage is predicted or detected, the method proceeds to step 116. Transition to step 116 may be automatic after the simulations or movements are performed in step 132, or transition to step 116 may require input from the surgical personnel, such as selecting "OK" or "DONE" on the displays 28, 29 with an input device to indicate to the OR Setup module 109 that the patient is in position.

Prior to step 114, the trackers 44, 46 may be setup according to the procedure outlined in U.S. Provisional Patent Application No. 61/753,219, filed on Jan. 16, 2013, entitled, "Tracking Devices and Navigation Systems and Methods for Use Thereof", hereby incorporated by reference, which may improve the likelihood that the trackers 44, 46 do not require repositioning during positioning in step 114.

The surgeon also has the ability to again review the design, confirm it matches the patient, and either give final approval or makes revisions in implant size, position, and/or orientation.

Instructions for placement of the machining station 56 are provided in step 116. One example of how these instructions are provided is shown in steps 136 through 142 in FIG. 9. Once the camera unit 36, patient, and trackers 44, 46 are properly positioned, the guidance station 20 can assist in guiding the machining station 56 into position relative to the bones to be machined. In step 136, the desired placement of the machining station 56 is shown on displays 28, 29. The cart 57 of the machining station 56 also has an integrated display 59 which is in communication with the guidance station 20 (see FIG. 1). The machining station display 59 additionally shows the desired placement of the machining station 56. The desired placement may be an overhead visual illustration of the cart 57 in a desired position, such as shown in FIGS. 6 and 7.

A position and orientation of the cart 57 is tracked by the guidance station 20 using the instrument tracker 48. More specifically, owing to rigid connections of the instrument tracker 48 to the end effector and the end effector to an arm/coupler structure of the machining station 56, the guidance station 20 is able to determine a position and orientation of the cart 57 based on the position and orientation of the instrument tracker 48 using: (1) joint angle data measured by position encoders located at joints in the machining station 56 and/or joint angle data calculated by a kinematics module, as described in U.S. Provisional Patent Application No. 61/679,258, entitled, "Surgical Manipulator Capable of Controlling a Surgical Instrument in either a Semi-Autonomous Mode or a Manual, Boundary Constrained Mode", the disclosure of which is hereby incorporated by reference; and (2) data relating to the arm/coupler structure (e.g., virtual model data) of the machining station 56, as described in U.S. Provisional Patent Application No. 61/679,258, entitled, "Surgical Manipulator Capable of Controlling a Surgical Instrument in either a Semi-Autonomous Mode or a Manual, Boundary Constrained Mode", the disclosure of which is hereby incorporated by reference. Alternatively, a separate tracker (not shown) is attached to and calibrated to a virtual model of the cart 57 to track a position and orientation of the cart 57.

Figure 9A:
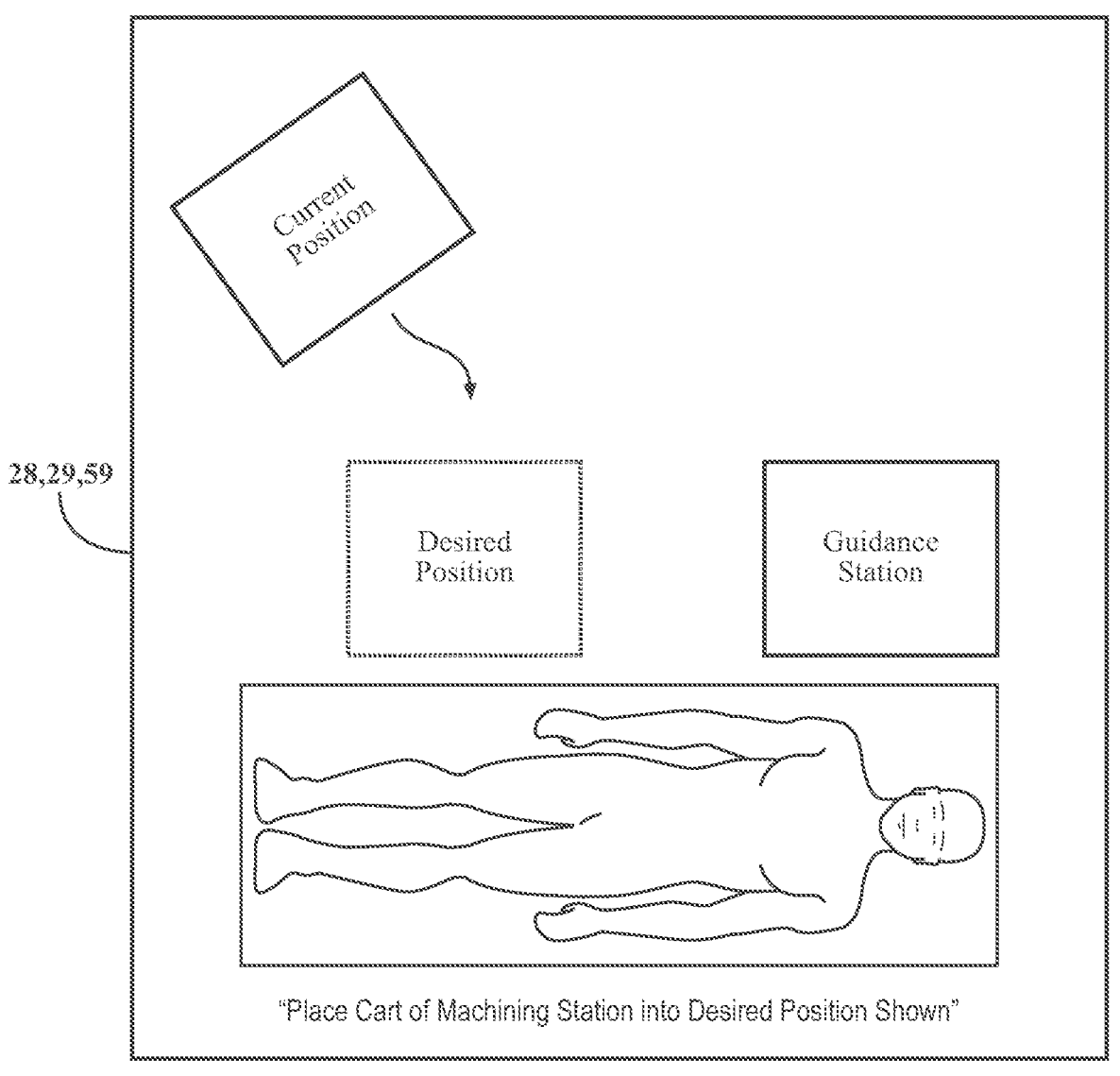
FIG. 9A is an illustration of a screen shot from the OR Setup software module providing instructions on placement of a machining station.

In either case, the displays 28, 29, 59 in some embodiments not only show the desired overhead position of the cart 57, but also the current position of the cart 57. One example of representations of the cart 57 shown on displays 28, 29, 59 is shown FIG. 9A. In FIG. 9A, one visual representation is an image of the cart 57 (represented by a 2-D rectangle) shown in the desired position. Another visual representation is an image of the cart 57 (represented by a 2-D rectangle) shown in the current position. The representation of the cart 57 in the current position moves on the displays 28, 29, 59 as the cart 57 is moved. Further instructions provided by the guidance station 20 may include geometric images, such as an arrow, guiding the surgical personnel as to the direction in which to move the cart 57 to reach the desired position.

In step 138, the surgical personnel place the machining station 56 in the desired position by watching the displays 28, 29, 59, and moving the cart 57 such that the visual representations on the displays 28, 29, 59 of the actual cart position moves toward the visual representation of the desired position. In step 140, the OR Setup module 109 checks the error between actual position and desired position until the cart 57 reaches the desired position. Once the actual position of the machining station 56 is within a predetermined tolerance of the desired position, as depicted by the visual representation of the actual position of the cart 57 being aligned with the visual representation of the desired position of the cart 57, i.e., the rectangles are aligned, the OR Setup module 109 indicates that the machining station 56 is in the desired position and moves to step 118. The visual images on the displays 28, 29, 59 may blink or provide some other visual effect when the cart 57 has reached the desired position.

In step 118, the guidance station 20 instructs the surgical personnel on their proper positions relative to the patient, machining station 56, guidance station 20, etc. This may be done by re-displaying the overhead layout, such as those shown in FIGS. 6 and 7. Once the surgical personnel are in position and ready, the procedure can be started—see step 106 in FIG. 4.

In some embodiments, the machining station 56 is a robotic surgical cutting system for cutting away material from a patient's anatomy, such as bone or soft tissue. Once the cutting system is determined to be in the proper position by the guidance station 20, the cutting system cuts away material to be replaced by surgical implants such as hip and knee implants, including unicompartmental, bicompartmental, or total knee implants. Some of these types of implants are shown in U.S. patent application Ser. No. 13/530,927, entitled, "Prosthetic Implant and Method of Implantation", the disclosure of which is hereby incorporated by reference. The guidance station 20 instructs the surgeon on proper procedures for locating these implants on bone and securing the implants in position, including the use of trial implants.

In other systems, the instrument 22 has a cutting tool that is movable in three degrees of freedom relative to a handheld housing and is manually positioned by the hand of the surgeon, without the aid of cutting jigs, guide arms or other constraining mechanism. Such systems are shown in U.S. patent application Ser. No. 13/600,888, entitled, "Surgical Instrument Including Housing, a Cutting Accessory that Extends from the Housing and Actuators that Establish the Position of the Cutting Accessory Relative to the Housing", the disclosure of which is hereby incorporated by reference.

In these embodiments, the system includes a hand held surgical cutting instrument having a cutting tool. A control system controls movement of the cutting tool in at least 3 degrees of freedom using internal actuators/motors, as shown in U.S. patent application Ser. No. 13/600,888, entitled, "Surgical Instrument Including Housing, a Cutting Accessory that Extends from the Housing and Actuators that Establish the Position of the Cutting Accessory Relative to the Housing", the disclosure of which is hereby incorporated by reference. The guidance station 20 communicates with the control system. One tracker (such as tracker 48) is mounted to the instrument. Other trackers (such as trackers 44, 46) are mounted to a patient's anatomy.

In this embodiment, the guidance station 20 communicates with the control system of the hand held surgical cutting instrument. The guidance station 20 communicates position and/or orientation data to the control system. The position and/or orientation data is indicative of a position and/or orientation of the instrument 22 relative to the anatomy. This communication provides closed loop control to control cutting of the anatomy such that the cutting occurs within a predefined boundary (the term predefined boundary is understood to include predefined trajectory, volume, line, other shapes or geometric forms, and the like).

In alternative embodiments the trackers 44, 46, 48 could be other line-of-sight tracking devices or non line-of-sight tracking devices used for navigation. The trackers 44, 46, 48 could employ sound waves, magnetic fields, RF signals, and the like to determine position and/or orientation. In some of these embodiments, step 110 relates to placement of sensing devices, transmitters, generators, etc. associated with these other types of navigation systems. Likewise, steps 130 and 132 relate to checking for obstructions or other interference with signals from these other types of navigation systems. In essence, surgical personnel are instructed to place trackers of the navigation system with respect to the patient's anatomy, regardless of the type of navigation employed, so that obstructions or interference is minimized or within acceptable tolerances.

In some embodiments, the objects may be arranged with respect to an operating room table that is fixed in the operating room, i.e., unable to be readily moved, except for adjustments of portions of the operating room table. In some embodiments, some or all of the objects to be arranged according to their desired placement may be located outside the operating room and first need to be moved into the operating room. In other embodiments, some or all of the objects to be arranged according to their desired placement may already be located inside the operating room, but not yet in their desired placements.

In some embodiments, pre-surgery is considered the time leading up to any cutting or incision of the patient in the operating room for purposes of treatment. Such cutting may include the cutting of skin and tissue to access the knee joint for purposes of knee replacement or the hip joint for purposes of hip replacement.

In some embodiments, arranging the objects in the operating room may be performed manually such as by pushing a wheeled cart of the object into position, or manually attaching trackers to the patient. In other embodiments, arranging the objects may include guiding the objects into their desired placement remotely or by some automated control, such as by moving an automated cart using associated steering controls.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A system for guiding arrangement of a robotic system in an operating room, the system comprising:

one or more controllers comprising a non-transitory computer-readable medium having stored thereon instructions that implement a software module for guiding arrangement of the robotic system in the operating room, the instructions, when executed by the one or more controllers configured to:

evaluate surgical procedure information; and determine a desired placement of the robotic system in the operating room based on the evaluation of the surgical procedure information;

a localizer configured to determine a current placement of the robotic system in the operating room; and a display disposed in the operating room and being coupled to the one or more controllers, the display being configured to display visual representations of the current placement and the desired placement of the robotic system to guide a user on manual placement of the robotic system in the operating room;

wherein the surgical procedure information includes one or more of: an identification of a bone to be treated; an identification of a desired implant to be attached to a bone; and a type of surgical procedure.

2. The system of claim 1, wherein the one or more controllers are configured to wirelessly receive the surgical procedure information.

3. The system of claim 1, further comprising a guidance station coupled to the localizer and the guidance station is configured to communicate with the one or more controllers and with the robotic system.

4. The system of claim 3, wherein the guidance station includes the display.

5. The system of claim 1, wherein the robotic system includes a tracking device, and wherein the localizer is configured to determine the current placement of the robotic system by further being configured to determine a position of the tracking device.

6. The system of claim 1, wherein the display is configured to display the visual representations of the current placement and the desired placement of the robotic system in an overhead layout.

7. The system of claim 1, wherein the display is configured to display a direction in which to move the robotic system in the operating room.

8. The system of claim 1, wherein the display is configured to display a visual effect in response to the robotic system reaching the desired placement.

9. The system of claim 1, wherein the display is configured to update the visual representation of the current placement of the robotic system in response to movement of the robotic system.

10. The system of claim 1, wherein the robotic system is further defined as a robotic cutting system that is configured to cut bone.

* * * * *